(12) United States Patent
Grabinsky et al.

(10) Patent No.: US 12,408,945 B2
(45) Date of Patent: Sep. 9, 2025

(54) INSERTION DEVICES

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Jessica Marie Grabinsky, Melrose, MA (US); Jeffrey Louis Barnes, Andover, MA (US); Carolyn Marie Krasniak, Andover, MA (US); Timothy Matthew Murray, Tiverton, RI (US); Kevin Michael Falco, Andover, MA (US); Francheska Torres, Charlton, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 331 days.

(21) Appl. No.: 17/889,844

(22) Filed: Aug. 17, 2022

(65) Prior Publication Data
US 2023/0000521 A1    Jan. 5, 2023

Related U.S. Application Data

(63) Continuation of application No. PCT/US2021/018221, filed on Feb. 16, 2021.
(Continued)

(51) Int. Cl.
*A61B 17/34* (2006.01)

(52) U.S. Cl.
CPC .. *A61B 17/3423* (2013.01); *A61B 2017/3484* (2013.01)

(58) Field of Classification Search
CPC ........ A61B 17/3423; A61B 2017/3484; A61B 17/3462; A61B 2017/3445; A61B 2017/349; A61B 17/3421
See application file for complete search history.

(56) References Cited

U.S. PATENT DOCUMENTS

| 5,147,316 A * | 9/1992 | Castillenti ..........  A61B 17/3421 604/174 |
| 5,217,441 A * | 6/1993 | Shichman ..........  A61B 17/3496 604/536 |

(Continued)

FOREIGN PATENT DOCUMENTS

| WO | 2019204425 A1 | 10/2019 |
| WO | 2021007327 A1 | 1/2021 |

OTHER PUBLICATIONS

International Preliminary Report on Patentability for International Application No. PCT/US2021/018221, date of mailing, Sep. 1, 2022.

(Continued)

*Primary Examiner* — Julian W Woo
(74) *Attorney, Agent, or Firm* — Seager, Tufte & Wickhem LLP

(57) ABSTRACT

A cannula for passing surgical instruments through tissue. In some instances, the cannula may include a distal flange flexible between a radial configuration and a longitudinal configuration. In some instances, the cannula may also include an actuator configured to move the distal flange between the radial configuration and the longitudinal configuration. In some instances, the cannula may include a (Continued)

valve disposed within the lumen of the cannula, and a cap configured to secure the valve to the cannula. The valve may include a body member having a base and first and second opposing walls extending from the base. In some instances, the valve has an arcuate cutout in the lower surface configured to fit around an instrument shaft inserted therethrough. In some instance, the cannula includes a slit extending an entire length of the cannular to permit an instrument shaft to be inserted and/or removed laterally.

6 Claims, 41 Drawing Sheets

Related U.S. Application Data

(60) Provisional application No. 63/020,309, filed on May 5, 2020, provisional application No. 62/991,968, filed on Mar. 19, 2020, provisional application No. 62/991,928, filed on Mar. 19, 2020, provisional application No. 62/977,879, filed on Feb. 18, 2020.

(56) References Cited

U.S. PATENT DOCUMENTS

| | | | |
|---|---|---|---|
| 5,716,369 A * | 2/1998 | Riza | A61B 17/34 606/139 |
| 8,038,652 B2 | 10/2011 | Morrison et al. | |
| 8,092,431 B2 | 1/2012 | Lunn et al. | |
| 8,377,089 B2 | 2/2013 | Lipchitz et al. | |
| 8,460,186 B2 * | 6/2013 | Ortiz | A61B 17/3421 600/216 |
| 9,131,958 B2 | 9/2015 | Lunn et al. | |
| 9,808,282 B2 * | 11/2017 | Spenciner | A61B 17/3421 |
| 10,052,090 B2 | 8/2018 | Lipchitz et al. | |
| 2011/0144447 A1 | 6/2011 | Schleitweiler et al. | |
| 2011/0144590 A1 | 6/2011 | Sakai, Jr. et al. | |
| 2012/0245426 A1 | 9/2012 | Salvas et al. | |
| 2019/0239922 A1 | 8/2019 | Pilgeram et al. | |

OTHER PUBLICATIONS

International Search Report and Written Opinion for International Application No. PCT/US2021/018221, date of mailing Jul. 9, 2021.

* cited by examiner

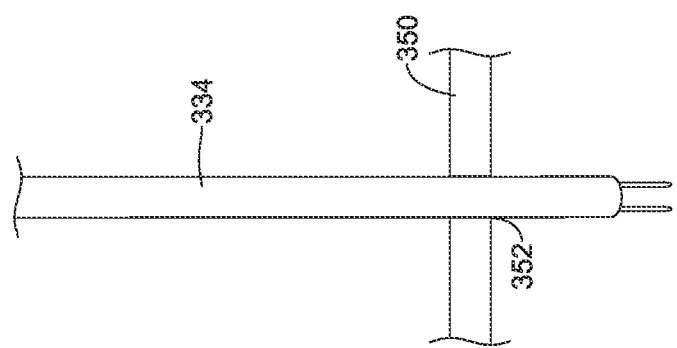
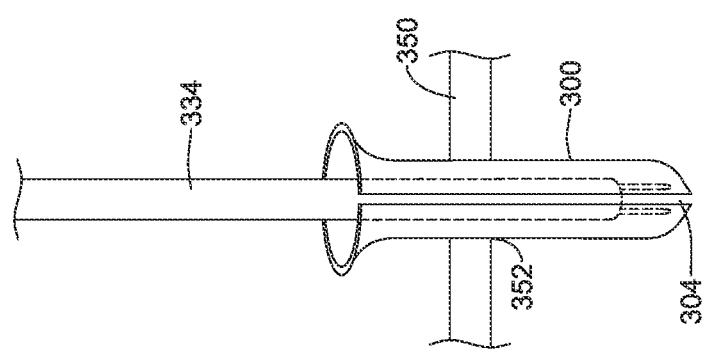
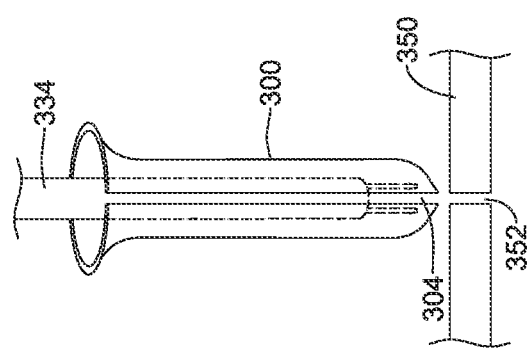

INSERTION DEVICES

CROSS REFERENCE TO RELATED APPLICATIONS

This application is a continuation of International Application No. PCT/US2021/018221, filed Feb. 16, 2021, titled INSERTION DEVICES INCLUDING CANNULAE AND ASSOCIATED DUCKBILL VALVES, which claims the benefit of and priority to U.S. Provisional Patent Application Ser. No. 62/977,879, filed on Feb. 18, 2020, titled ACTUATABLE CANNULA, U.S. Provisional Patent Application Ser. No. 62/991,968, filed on Mar. 19, 2020, titled DUCKBILL VALVE, U.S. Provisional Patent Application Ser. No. 62/991,928, filed Mar. 19, 2020, titled FLEXIBLE CANNULA WITH OBTURATOR, and U.S. Provisional Patent Application Ser. No. 63/020,309, filed May 5, 2020, titled REGENETEN NEXTGEN MULTISHOT TENDON ANCHOR INSERTER CANNULA, the disclosures of which are incorporated herein by reference.

BACKGROUND

Arthroscopic and endoscopic surgical procedures allow closed surgery to be performed via portals through which a variety of instruments may be passed to gain access to an internal surgical work site. Accordingly, a cannula may be used to pass instruments into the surgical work site. Furthermore, many arthroscopic procedures require the use of fluid to distend and irrigate the joint being operated upon, so in such instances the cannula must provide a sealed passageway in order to enable instruments to be passed into and out of the cannula while maintaining a fluid seal whether or not an instrument is in the cannula passageway.

SUMMARY

This disclosure provides design, material, and use alternatives for medical devices for arthroscopic or endoscopic procedures.

An example cannula for passing surgical instruments through tissue includes an elongated body having a first end, a second end, and a lumen extending along a longitudinal axis therebetween, a first flange extending radially outward from the first end, a second flange extending radially outward from the second end, the second flange configured to move between a first radially oriented configuration and a second longitudinally oriented configuration, and an actuator configured to move the second flange between the first radially oriented configuration and the second longitudinally oriented configuration.

Alternatively or additionally to the embodiment above, the second flange is biased in the first radially oriented configuration.

Alternatively or additionally to the embodiments above, the first radially oriented configuration is an equilibrium position.

Alternatively or additionally to any of the embodiments above, the second flange includes a plurality of notches cut into an outer perimeter thereof, wherein when the second flange is moved to the second longitudinally oriented configuration, edges of the second flange between adjacent notches move together, narrowing gaps defined by the notches.

Alternatively or additionally to any of the embodiments above, the second flange includes a plurality of apertures disposed adjacent the elongated body.

Alternatively or additionally to any of the embodiments above, the actuator includes a shaft and a clamp, the shaft extending along the elongated body and the clamp attached to the shaft and extending at least partially around the elongated body.

Alternatively or additionally to any of the embodiments above, the shaft extends through a hole in the first flange.

Alternatively or additionally to any of the embodiments above, the clamp is slidable along the elongated body to move the second flange from the first radial configuration to the second longitudinally oriented configuration.

Alternatively or additionally to any of the embodiments above, the actuator is configured to be actuated by applying a longitudinal force on a portion of the shaft extending longitudinally above the first flange.

Alternatively or additionally to any of the embodiments above, the longitudinal force applied to the shaft moves the shaft and clamp longitudinally along the elongated body, the clamp moving the second flange into the second longitudinally oriented configuration.

Alternatively or additionally to any of the embodiments above, the elongated body is cylindrical and the clamp extends at least partially around a circumference of the elongated body.

Alternatively or additionally to any of the embodiments above, the elongated body is cylindrical and the clamp is an annular collar extending at least partially around a circumference of the elongated body.

Alternatively or additionally to any of the embodiments above, the actuator includes a plurality of shafts spaced apart around the elongated body and connected to the clamp.

Alternatively or additionally to any of the embodiments above, the cannula further includes a ring connecting the plurality of shafts above the first flange.

Alternatively or additionally to any of the embodiments above, the cannula further includes a first valve disposed within the elongated body.

Alternatively or additionally to any of the embodiments above, the first flange includes a second valve.

Another example cannula for passing surgical instruments through tissue includes a tubular body defining a lumen, a first flange extending radially outward from a first end of the tubular body, a second flange extending radially outward from a second end of the tubular body, the second flange having a plurality of notches cut into an outer perimeter thereof, and an actuator slidably coupled to the tubular body and configured to move the second flange from a first configuration in which the second flange extends radially outward from the tubular body, to a second configuration in which the second flange extends longitudinally away from the second end of the tubular body.

Alternatively or additionally to any of the embodiments above, the actuator includes at least one shaft extending along an outer surface of the tubular body, and a clamp attached to the shaft, the clamp extending around at least a portion of an outer circumference of the tubular body.

Alternatively or additionally to any of the embodiments above, a first end of the shaft extends through an opening in the first flange and the clamp is attached to a second end of the shaft, wherein applying a longitudinal force to the first end of the shaft moves the shaft along the tubular body and the clamp pushes the second flange from the first configuration into the second configuration.

Alternatively or additionally to any of the embodiments above, the tubular body includes at least a first valve.

Alternatively or additionally to any of the embodiments above, the first flange includes a second valve.

A further example cannula for passing surgical instruments through tissue includes a tubular body having a first end and a second opposite end, the tubular body defining a longitudinal lumen extending between the first and second ends, a first flange extending radially outward at the first end of the tubular body, a second flange disposed at the second end of the tubular body, the second flange biased in a first configuration in which the second flange extends radially outward from the tubular body, the second flange moveable to a second configuration in which the second flange collapses radially inward and distal of the tubular body, wherein when in the second configuration, the second flange has an outer diameter substantially the same as an outer diameter of the tubular body, and an actuator slidably coupled to the tubular body, the actuator configured to move the second flange from the first configuration to the second configuration.

An example cannula for passing surgical instruments through tissue includes an elongated body having a distal end, a proximal end, and a lumen extending along a longitudinal axis therebetween, a flange extending radially outward from the distal end, a valve disposed within the lumen of the elongated body adjacent the proximal end, and a cap configured to be disposed over the proximal end of the elongated body, the cap configured to secure the valve to the elongated body, the cap engaging the valve to create a non-compressive seal therebetween.

Alternatively or additionally to the embodiment above, a proximal surface of the valve has a first mating geometry and an inner surface of the cap has a second mating geometry, wherein the non-compressive seal is created between the valve and cap when the first mating geometry of the valve engages the second mating geometry of the cap.

Alternatively or additionally to the embodiments above, the first mating geometry of the valve includes at least one ridge and the second mating geometry of the cap includes at least two ridges separated by a channel, wherein when the cap engages the valve, the at least one ridge on the valve is received within the channel on the cap.

Alternatively or additionally to the embodiments above, the first mating geometry of the valve includes two ridges separated by a channel and the second mating geometry of the cap includes three ridges separated by two channels, wherein when the cap engages the valve, the two ridges on the valve are received within the two channels on the cap.

Alternatively or additionally to the embodiments above, the cap is more flexible than the elongated body and the valve.

Alternatively or additionally to the embodiments above, the elongated body is cylindrical and includes threading or a plurality of circumferential ribs disposed on an outer surface of the elongated body, the cannula further including a nut extending around a circumference of the elongated body, the nut configured to selectively engage the threading or ribs and to move between a first position in which the nut is disengaged from the threading or ribs, allowing the nut to slide axially along the elongated body, and a second position in which the nut engages the threading or ribs.

Alternatively or additionally to the embodiments above, the threading or ribs are discontinuous and include at least one gap, the gaps of adjacent threads or ribs aligned longitudinally along a portion of the elongated body, wherein the nut has an inner circumference sized to move over the threading or ribs and at least one inwardly extending rigid projection, wherein when the nut is rotated such that the projection is aligned with the gaps, the nut slides axially along the elongated body, and when the nut is rotated such that the projection is not aligned with the gaps, the projection engages the threading or ribs and prevents the nut from moving axially along the elongated body.

Alternatively or additionally to the embodiments above, the cannula further includes a stop disposed adjacent each gap, the stop configured to limit rotation of the projection.

Alternatively or additionally to the embodiments above, the stop is an outwardly extending protrusion on the body.

Alternatively or additionally to the embodiments above, the stop is a recess in an outer surface of the body, the recess configured to receive a portion of the projection.

Alternatively or additionally to the embodiments above, the elongated body includes threading on the outer surface thereof, wherein the nut has an inner circumference sized to move over the threading and at least one inwardly extending rigid projection configured to engage the threading on the outer surface of the elongated body such that rotation of the nut allows the nut to move axially along the elongated body.

Alternatively or additionally to the embodiments above, the threading includes a plurality of discontinuous helical turns with a gap in each helical turn, the gaps aligned longitudinally, wherein when the nut is rotated such that the projection is aligned with the gaps, the nut slides axially along the elongated body without rotating, and when the nut is positioned between adjacent ribs and rotated such that the projection is not aligned with the gaps, the at least one projection engages the threading, requiring the nut to be rotated in order to move axially along the elongated body.

Alternatively or additionally to the embodiments above, the flange is wedge shaped with a flat proximal surface and an angled distal surface.

Another example cannula for passing surgical instruments through tissue includes an elongated body having a distal end, a proximal end, and a lumen extending along a longitudinal axis therebetween, a valve disposed within the lumen of the elongated body adjacent the proximal end, and a cap configured to be disposed over the proximal end of the elongated body, the cap configured to secure the valve to the elongated body, wherein a proximal surface of the valve has a first mating geometry and an inner surface of the cap has a second mating geometry, wherein a seal is created between the valve and cap when the first mating geometry of the valve engages the second mating geometry of the cap, wherein the proximal surface of the valve and the inner surface of the cap are both non-linear.

Alternatively or additionally to the embodiment above, the elongated body is cylindrical and includes threading or a plurality of circumferential ribs disposed on an outer surface of the elongated body, the cannula further including a nut extending around a circumference of the elongated body, the nut configured to selectively engage the threading or ribs and to move between a first position in which the nut is disengaged from the threading or ribs, allowing the nut to slide axially along the elongated body, and a second position in which the nut engages the threading or ribs.

Alternatively or additionally to the embodiments above, the threading or ribs are discontinuous and include a plurality of gaps aligned longitudinally along the elongated body, wherein the nut has an inner circumference sized to move over the threading or ribs and at least one inwardly extending rigid projection, wherein when the nut is rotated such that the projection is aligned with the gaps, the nut slides axially along the elongated body, and when the nut is rotated such that the projection is not aligned with the gaps, the projection engages the threading or ribs.

Alternatively or additionally to the embodiments above, the cannula further includes a stop disposed adjacent each gap, the stop configured to limit rotation of the rigid projection.

Another example cannula for passing surgical instruments through tissue includes an elongated cylindrical body having a distal end, a proximal end, and a lumen extending along a longitudinal axis therebetween, the elongated cylindrical body including threading or a plurality of circumferential ribs disposed on an outer surface of the elongated cylindrical body, a nut extending around a circumference of the elongated cylindrical body, the nut configured to selectively engage the threading or ribs and to move between a first position in which the nut is disengaged from the threading or ribs, allowing the nut to slide axially along the elongated body, and a second position in which the nut engages the threading or ribs, at least one valve disposed within the lumen of the elongated body adjacent the proximal end, and a cap configured to be disposed over the proximal end of the elongated body, the cap configured to secure the at least one valve to the elongated body, the cap engaging the at least one valve to create a non-compressive seal therebetween.

Alternatively or additionally to the embodiment above, the threading or ribs are discontinuous and include a plurality of gaps aligned longitudinally along the elongated body, wherein the nut has an inner circumference sized to move over the threading or ribs and at least one inwardly extending rigid projection, wherein when the nut is rotated such that the projection is aligned with the gaps, the nut slides axially along the elongated cylindrical body, and when the nut is rotated such that the projection is not aligned with the gaps, the projection engages the threading or ribs.

Alternatively or additionally to the embodiments above, the cannula further includes a stop disposed adjacent each gap, the stop configured to limit rotation of the rigid projection.

Another exemplary embodiment is an access cannula. The access cannula includes an elongate body defining an access lumen extending therethrough and a valve disposed in the access lumen. The valve includes a body member having a base and first and second opposing walls extending from the base. The first and second walls have first ends spaced apart at the base and second ends converging at a lower surface. The lower surface has a length and includes a slit extending at least partially along the length of the lower surface. The body member defines an axial passageway from the base to the lower surface through the slit. The valve also includes an arcuate cutout in the lower surface centered on a central axis of the body member. The arcuate cutout has a radius less than half the length of the lower surface of the first and second walls.

Alternatively or additionally to any embodiment herein, a length of the slit is less than the length of the lower surface.

Alternatively or additionally to any embodiment herein, a length of the slit is 4 times or less than the radius of the arcuate cutout.

Alternatively or additionally to any embodiment herein, the length of the slit is less than or equal to twice the radius of the arcuate cutout.

Alternatively or additionally to any embodiment herein, the lower surface is substantially perpendicular to the central axis.

Alternatively or additionally to any embodiment herein, the inner surfaces of the first and second walls are devoid of projections or depressions.

Alternatively or additionally to any embodiment herein, a depth of the arcuate cutout is equal to the radius of the arcuate cutout.

Alternatively or additionally to any embodiment herein, a depth of the arcuate cutout is greater than the radius of the arcuate cutout.

Alternatively or additionally to any embodiment herein, the first and second walls have a constant wall thickness from their first ends to their second ends.

Alternatively or additionally to any embodiment herein, a lower end face of each of the first and second walls has a constant wall thickness from a first end of the slit, along the arcuate cutout to a second end of the slit.

Alternatively or additionally to any embodiment herein, the base includes a circumferential flange extending beyond a width of the body member.

Alternatively or additionally to any embodiment herein, the radius of the arcuate cutout is between 0.05 inches and 0.2 inches.

Alternatively or additionally to any embodiment herein, the length of the lower surface is between 0.5 inches and 1 inch.

Another exemplary embodiment is an access cannula including an elongate body defining an access lumen extending therethrough and a duckbill valve disposed in the access lumen. The duckbill valve includes a body member having a base and first and second opposing walls having first ends spaced apart at the base and second ends converging at a lower surface. The lower surface has a length and includes a slit extending only partially along the length of the lower surface. The body member defines an axial passageway from the base to the lower surface through the slit. The inner surfaces of the first and second walls are devoid of projections or depressions. The valve also includes an arcuate cutout in the second ends of the first and second walls. The arcuate cutout has a radius less than half the length of the lower surface of the first and second walls.

Alternatively or additionally to any embodiment herein, a length of the slit is 4 times or less than the radius of the arcuate cutout.

Alternatively or additionally to any embodiment herein, the lower surface is substantially perpendicular to a central axis of the body member.

Alternatively or additionally to any embodiment herein, the first and second walls have a constant wall thickness from their first ends to their second ends.

Alternatively or additionally to any embodiment herein, a lower end face of each of the first and second walls has a constant wall thickness from a first end of the slit, along the arcuate cutout to a second end of the slit.

Alternatively or additionally to any embodiment herein, the radius of the arcuate cutout is between 0.05 inches and 0.2 inches and the length of the lower surface is between 0.5 inches and 1 inch.

Yet another exemplary embodiment is an access cannula including an elongate body defining an access lumen extending therethrough and a duckbill valve disposed in the access lumen. The duckbill valve includes a body member having a base and first and second opposing walls having first ends spaced apart at the base and second ends converging at a lower surface. The lower surface has a length. A slit is located between the second ends of the first and second opposing walls at the lower surface. The slit has a length less than the length of the lower surface such that the slit extends only partially along the length of the lower surface. The body member defines an axial passageway from the base to the lower surface through the slit. The valve also includes an arcuate cutout in the second ends of the first and second walls. The arcuate cutout has a length measured along the length of the lower surface of the first and second walls. The length of the slit is less than or equal to the length of the arcuate cutout.

A further exemplary embodiment is a cannula comprising a flexible shaft having a distal end and a proximal end and a slit extending between the distal end and the proximal end.

Alternatively or additionally to any embodiment herein, the proximal end of the flexible shaft may be flared.

Yet a further exemplary embodiment is a cannula comprising a flexible shaft having a distal end and a proximal end, a slit extending along an entire length of the flexible shaft from the distal end to the proximal end, and a flared region located at the proximal end. The cannula is configured to be positionable around an elongate shaft of a medical device to be inserted through an incision simultaneously with the elongate shaft of the medical device acting as an obturator and then removed therefrom by passing the elongate shaft of the medical device laterally through the slit.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 33A-33C illustrate steps of inserting the combination of the cannula and tissue stapler of FIG. 32 into an incision of a patient.

DETAILED DESCRIPTION

Figure 1:
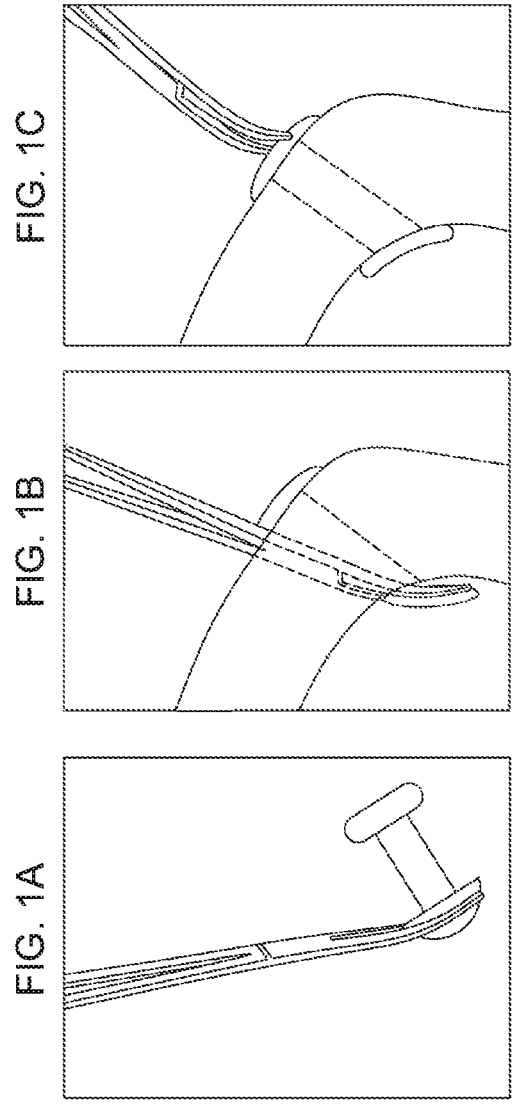
FIGS. 1A, 1B, and 1C illustrate the insertion of a prior art cannula.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

During arthroscopic surgeries, such as rotator cuff repair surgery, visualization can be an issue due to limited real estate in the subacromial space. Proper cannula placement and in-vivo pressure can vastly improve the surgeon's ability to visualize the proper anatomy. The soft tissue in the subacromial space can hinder visualization by collapsing inward if proper pressure is not held within the joint space. Cannulas with sufficient valve systems can hold pressure within the joint space and allow the surgeon to operate freely without visualization issues.

An arthroscopic fluid pump may be used to provide fluid distension to increase visibility and instrument navigation in the surgical site. The loss of fluid distension caused by leakage from surgical portals created to pass medical instruments into the surgical site is a problem often associated with the use of fluid distension and conventional cannulas. Excessive loss of fluid distention through these portals may lead to reduced visibility, reduced working space, and require the surgeon to increase fluid pressure output from the arthroscopic pump. Increasing fluid pressure is not desirable as it may increase the risk for patient complications. Rigid surgical cannulas have been used to prevent loss of fluid distention while allowing medical instruments to be passed through the surgical portals as needed. However, rigid cannulas may restrict instrument mobility, working space, and cause unintended damage to the patient.

Proper cannula placement and in-vivo pressure can vastly improve the surgeon's ability to visualize the proper anatomy. The soft tissue in the subacromial space can hinder visualization by collapsing inward if proper pressure is not held within the joint space. Cannulas with sufficient valve systems can hold pressure within the joint space and allow the surgeon to operate freely without visualization issues.

Prior art silicone cannulas are available in several lengths and diameters to account for different anatomies and surgeon preferences. These cannulas are made of a flexible material to protect the anatomy during insertion and removal into the joint space. These cannulas have a distal flange to retract the soft tissue around the insertion area to improve visualization. They may have one or more valves to improve fluid dynamic capability.

The prior art cannulas are often I-shaped, requiring the surgeon to fold the distal or inner flange in half and grasp it with an instrument such as a hemostat (FIG. 1A), insert the combined hemostat and cannula through the skin incision and into the joint space (FIG. 1B), and release and retract the hemostat (FIG. 1C). However, the use of the hemostat may be awkward for insertion and may necessitate a larger skin incision than would be required for the insertion of a cylindrical or T-shaped cannula.

Figure 2:
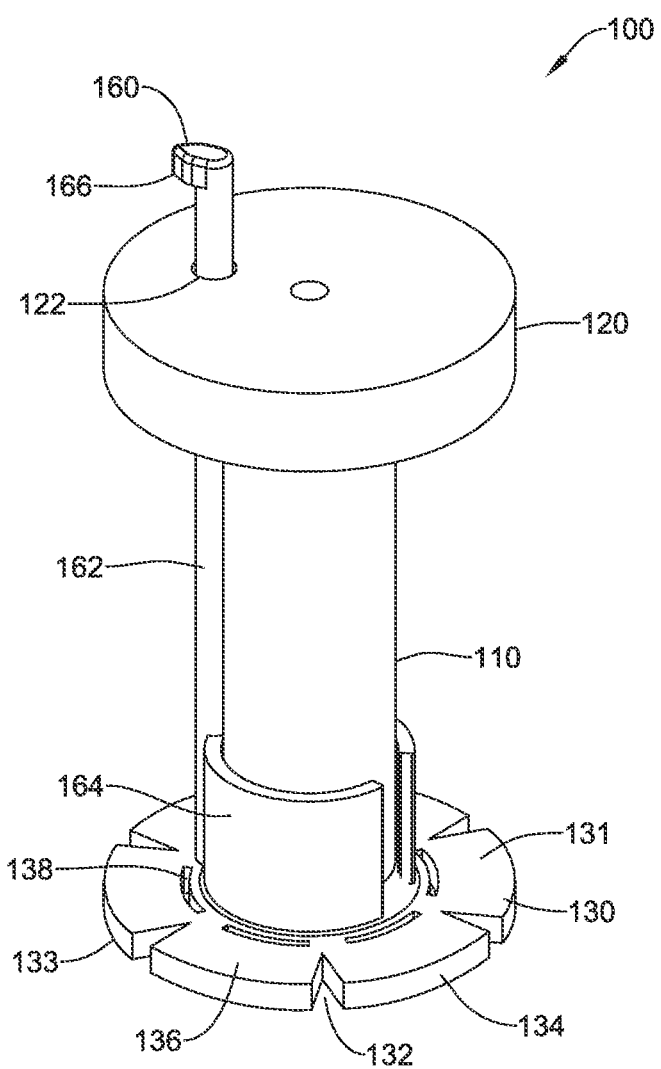
FIG. 2 is a perspective view of an exemplary cannula.

A cannula with a distal flange having relief slits or notches so the distal flange may transition from a distal flanged I-shaped cannula to a standard T-shaped cylindrical cannula has the advantage of being insertable into a skin incision without the use of a hemostat or other tool. Such a cannula 100 is shown in FIG. 2. The cannula 100 may include an elongated body 110 having a longitudinal axis, with a proximal flange 120 disposed at a first end of the body 110, and a distal flange 130 disposed at a second end of the body 110, and an actuator 160. The body 110 defines a lumen 111 extending along the longitudinal axis (see FIG. 6). When inserted into a skin incision, the proximal flange 120 may sit outside the joint space, on the skin, and serve as the entry point for the necessary devices for the procedure. The distal flange 130 may sit inside the joint space and retract surrounding soft tissue to improve visualization inside the joint space. The body 110 is illustrated as a cylinder, with a round cross-section, however it will be understood that the cross-sectional shape of the body 110 may be another shape, such as, but not limited to, oval, teardrop, stadium, etc.

The proximal flange 120 may extend radially outward from the first end of the body 110, and the distal flange 130 may extend radially outward from the second end of the body 110. The proximal flange 120 may help prevent over-insertion of the cannula 100 during the insertion process because the proximal flange 120 may be thicker than the distal flange 130. The thicker proximal flange 120 may be difficult to fold or bend and pass through the incision and into the body. In an exemplary embodiment only, the thickness of the proximal flange 120 may be about twice the thickness of the distal flange 130. Each of the proximal flange 120 and distal flange 130 may be generally circular as illustrated, or oval, teardrop, or stadium in shape, and may have similar or different shapes and diameters.

The body 110, proximal flange 120, and distal flange 130 may be a monolithic element, formed as a single piece. In other examples, one or more of the body 110, proximal flange 120, and distal flange 130 may be formed from different materials. In one example, the body 110, proximal flange 120, and distal flange 130 are formed as a monolithic structure, made of a flexible polymeric material such as silicone or polyurethane.

Figure 3:
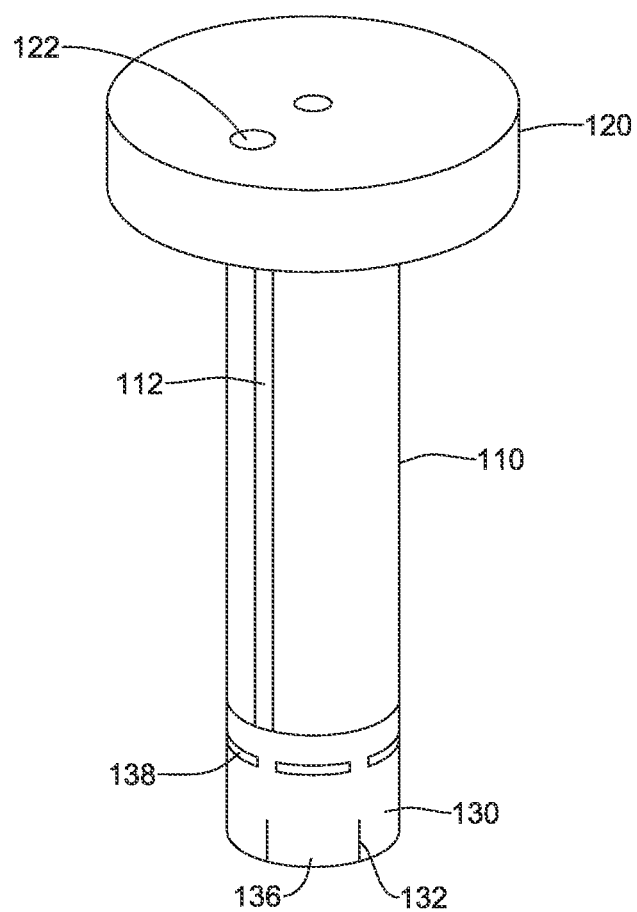
FIG. 3 is a perspective view of the cannula of FIG. 2 without the actuator and with the distal flange in the second configuration.

The distal flange 130 may have relief elements so that the flange may easily bend back and forth between a first radial configuration in which the distal flange 130 extends radially outward from the body 110, as shown in FIG. 2, and a second longitudinal configuration in which the distal flange 130 is bent such that it extends longitudinally from the body 110, as shown in FIG. 3. The distal flange 130 is biased in the first radial configuration. The actuator 160 is not shown in FIG. 3 in order to illustrate the configuration of the distal flange 130, which may be substantially covered by the actuator 160 in the second configuration. In one example, the relief elements include a plurality of notches 132 cut into the outer perimeter 134 of the distal flange 130. The notches 132 may extend radially inward from the outer perimeter 134 of the distal flange 130 at spaced apart circumferentially arranged locations. In some instances, the notches 132 may be triangular cuts with the widest part of the cut at the perimeter 134 of the distal flange 130, as shown in FIG. 2. In other embodiments, the notches 132 may be circular, oval, or teardrop in shape, for example. The width and depth of each notch 132 as well as the number of notches 132 distributed around the distal flange 130 may be selected to achieve a flange with sufficient integrity to maintain the first radially extended configuration when not compressed by the actuator, while still allowing the actuator 160 to move the distal flange 130 into the second configuration. In some instances, as adjacent sections 136 of the distal flange 130 move (e.g., bend, flex or deflect) into the second configuration, the notches 132 narrow until adjacent sections 136 are in direct contact with one another, creating a substantially tubular structure, as shown in FIG. 3.

The relief elements may also include a plurality of apertures 138 extending transversely through the distal flange 130 from a proximal surface 131 to a distal surface 133 of the distal flange 130. The apertures 138 may encourage the sections 136 of the distal flange 130 to pivot and bend/flex around the apertures 138 when pushed by the actuator 160. The apertures 138 may be positioned circumferentially near the inner edge of the distal flange 130, adjacent the body 110. In some examples, each section 136 includes an aperture 138 proximate the base of the section 136. The apertures 138 may be curved and may have a length extending along a majority of the inner portion of each section 136, as illustrated in FIG. 2. In some examples, the distal flange 130 may have both notches 132 and apertures 138. In some instances, the notches 132 may extend radially toward the radial position of the apertures 138 from the perimeter 134. In some instances, the radial length of the notches 132 may be less than the radial distance between the perimeter 134 and the circumferentially arranged apertures 138.

At least the distal flange 130 may be comprised of a flexible polymeric material such as silicone or polyurethane, so that it may transition easily from a radially extending flange (FIG. 2) to a cylindrical wall (FIG. 3) having a radial extent less than the radial extent of the distal flange 130 in its radially extended configuration (FIG. 2), when acted upon by the actuator 160.

The distal flange 130 may be moved from the first, radially extended configuration to the second, deflected configuration through actuation of the actuator 160, such as by axial sliding movement of the actuator 160. The actuator 160 may include a shaft 162, a clamp 164, and a head 166. The actuator 160 may be provided with the cannula 100, such as included as an indispensable component of the cannula 100. The shaft 162 may extend from the clamp 164 along a length of the body 110 of the cannula 100, such that the medical personnel can manipulate the actuator 160 from the proximal end of the cannula 100 to cause the clamp 164 to bend or flex the distal flange 130 during use. For example, the shaft 162 may extend through a hole 122 in the proximal flange 120, and along the body 110. In some examples, the body 110 may have a longitudinal depression or groove 112 configured to receive the shaft 162 therealong. See FIG. 3. The proximal end of the shaft 162 may extend proximally or above the proximal flange 120, and may have a head 166 larger than the shaft 162 to receive the user's thumb or finger for pushing or otherwise actuating the shaft 162. The head 166 may also include ridges, grooves, or other texture to assist the user in grasping the head 166 to pull the actuator 160 proximally and release the distal flange 130 once the cannula 100 has been inserted. The distal end of the shaft 162 is attached or fixed to the clamp 164. The clamp 164 may extend at least partially around the body 110. In some examples, the body 110 is cylindrical and the clamp 164 may be an annular shaped collar extending partially or completely around the circumference of the body 110. The shaft 162 and clamp 164 are slidable along the body 110 from a first position in which the distal flange 130 is in the first, radially extended configuration, to a second position in which the distal flange 130 is in the second, radially collapsed configuration. In some instance, the first, radially extended configuration may be an equilibrium position in which the distal flange 130 is not subjected to an external force, and the second, radially collapsed configuration may be a deflected position in which the distal flange 130 is subjected to an external force (i.e., a collapsing force applied by the clamp 164.

Figure 4:
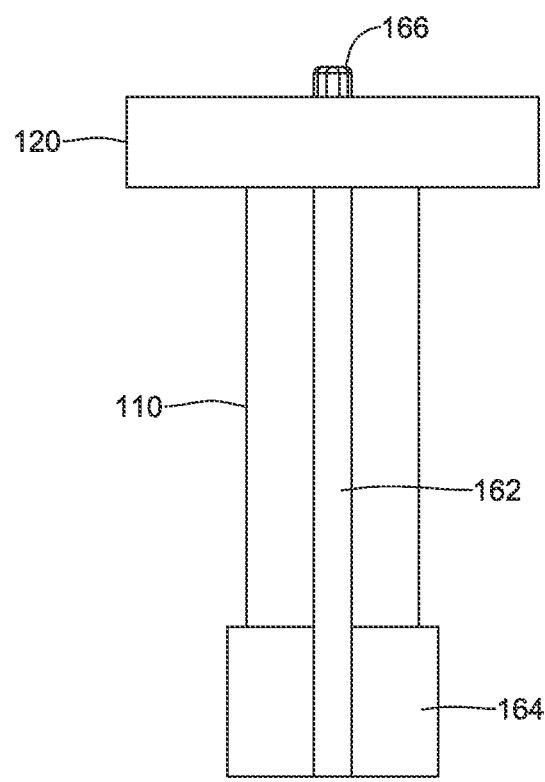
FIG. 4 is a side view of the cannula of FIG. 2 with the actuator in the second position.

When the cannula 100 is to be inserted into a skin incision, the actuator 160 may be actuated to collapse the distal flange 130 radially inward to facilitate passage of the distal flange 130 through an incision or other portal gaining access to an interior cavity or anatomical space of a patient. For example, a longitudinal force is applied distally onto the head 166 of the shaft 162, which slides the shaft 162 and clamp 164 longitudinally along the body 110, bending or deflecting the distal flange 130 into the second configuration, in which the distal flange 130 collapses radially inward and distally such that the distal flange 130 extends longitudinally and parallel to the central axis of the body 110. See FIG. 3. The head 166 may prevent the shaft 162 from sliding through the proximal flange 120. When the actuator 160 is in the second position, the head 166 may move toward the proximal flange 120 (e.g., the head 166 may rest on the proximal flange 120) and the clamp 164 may cover (e.g., extend over, circumferentially surround, etc.) the distal flange 130, as shown in FIG. 4. With the cannula 100 in the second configuration, the surgeon may deliver the cannula 100 into the joint space without the need to clamp the distal flange into a hemostat. When the cannula 100 is successfully in the joint space, the user will pull proximally on the head 166 of the actuator 160, moving the actuator 160 back to the first position to release the distal flange 130 back into its first, radially extended configuration, as shown in FIG. 2.

Figure 5:
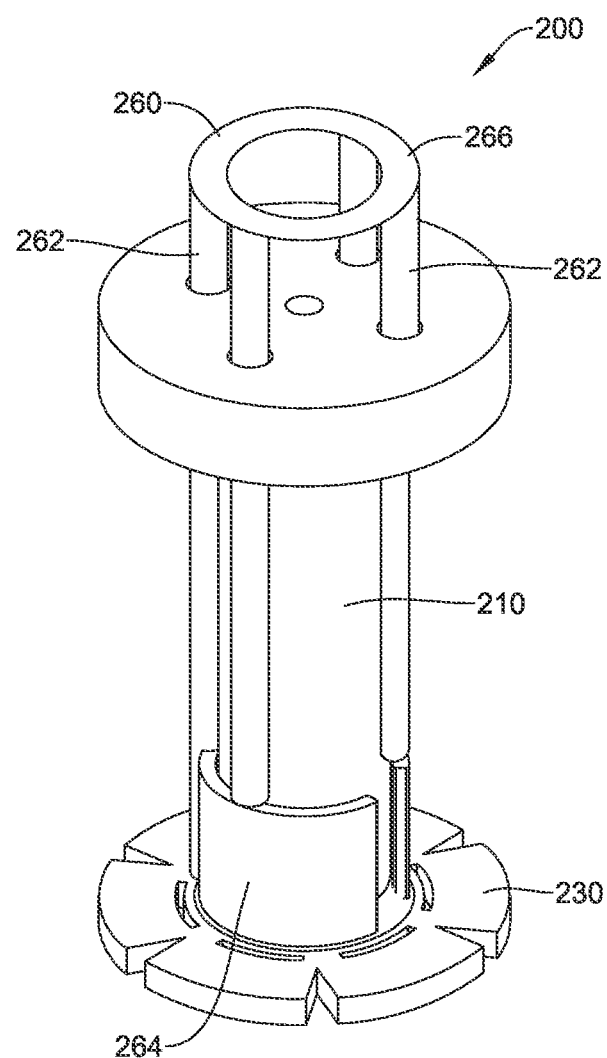
FIG. 5 is a perspective view of another exemplary cannula.

In another embodiment, the cannula 200 may include an actuator 260 with a plurality of shafts 262 spaced apart around the body 210 and connected to the clamp 264, as shown in FIG. 5. The proximal ends of each shaft 262 may be connected to a ring 266. The ring 266 may allow the surgeon to easily push all of the shafts 262 simultaneously, thereby providing a substantially equal longitudinal force on each shaft 262. The plurality of shafts 262 may then provide an equal force around the circumference of the distal flange 230, which may be advantageous when the distal flange 230 is thicker, has a greater diameter, or is stiffer.

Figure 6:
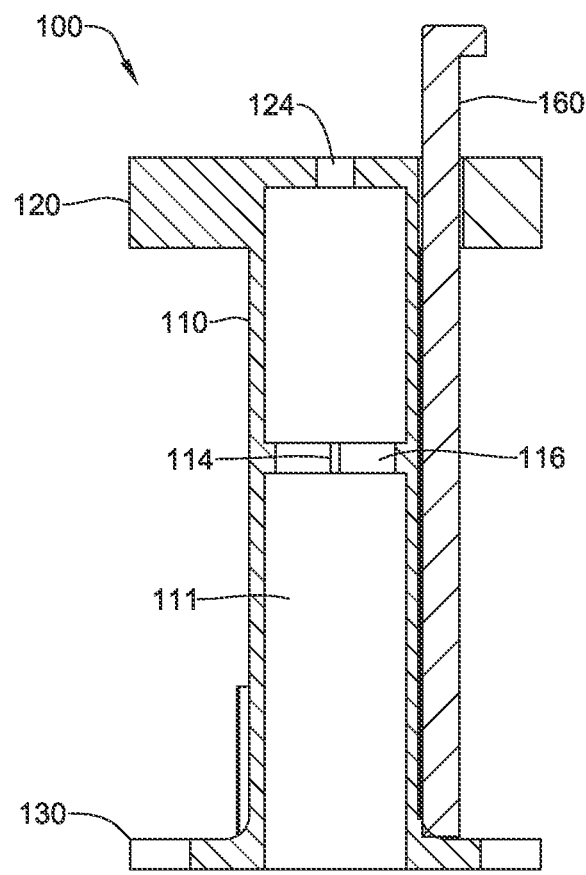
FIG. 6 is a side cross-sectional view of the cannula of FIG. 2.
Figure 7:
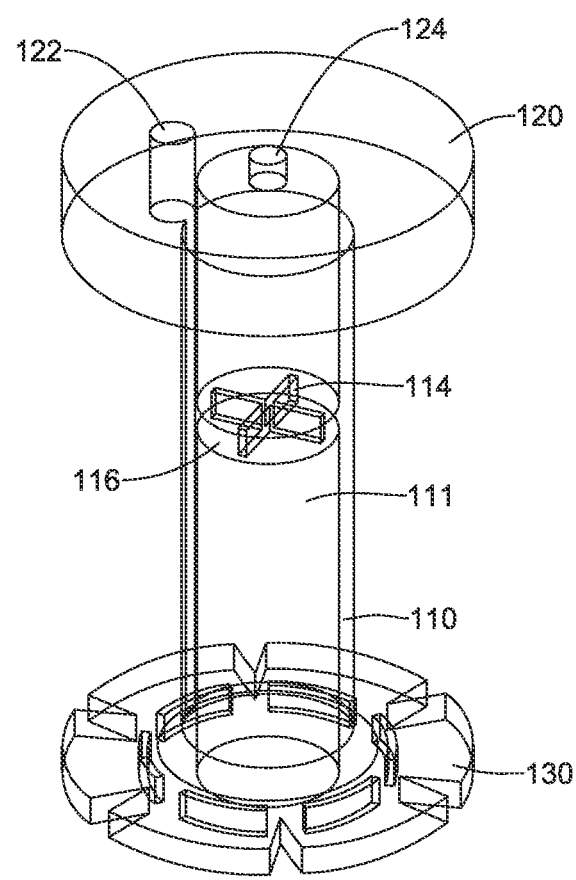
FIG. 7 is a perspective transparent view of the cannula of FIG. 2 without the actuator.

The cannula 100 may include at least one valve configured to prevent or limit the amount of fluid escaping through the lumen 111 of the cannula and to maintain the hydrostatic pressure inside the joint space. A first valve 114 may be located within the body 110 between the proximal flange 120 and the distal flange 130, as shown in FIG. 6. The first valve 114 may prevent fluid from exiting out of the body when instruments are being inserted through the cannula 100. The first valve 114 within the body 110 may be formed by one or more slits in a transverse member 116 extending across the lumen 111. The first valve 114 may be formed by a single slit or two slits forming a cross. In some embodiments, a second valve 124 may be located in the proximal flange 120 to prevent fluid from exiting the body when the cannula 100 itself is being inserted into the body. The second valve 124 within the proximal flange 120 may be formed by one or more slits or a small opening extending through the proximal flange 120 into the lumen 111 of the body 110. FIG. 7 is a transparent illustration of the cannula 100 with the actuator removed for clarity, showing the first valve 114 as two slits in the transverse member 116 forming a cross, and the second valve 124 as a small hole in the center of the proximal flange 120.

The transverse member 116 defining the first valve 114 may be made from a polymer material such as silicone, to substantially reduce the amount of tearing or wear as a result of insertion and/or withdrawal of sharp instruments. The transverse member 116 may be formed by injection molding, thus the entire cannula 100 may be made of the same material, such as silicone or polyurethane. In another example, at least the transverse member 116 may be made of polyisoprene. In another example, the body 110, proximal flange 120, and distal flange 130 may also be made of polyisoprene, such that the entire cannula 100 is made of a single material. Other natural or synthetic materials known to one of ordinary skill in the art, and that would substantially reduce the amount of tear or wear, could also be used for any or all of the transverse member 116, body 110, proximal flange 120, and distal flange 130. These materials include, but are not limited to, silicone, rubber, vinyl, polyurethane elastomers, or a combination of components, including styreneethylene-butylene-styrene (SEBS) block co-polymers, polyolefins, mineral oils, and silicone oils. All elements except the actuator 160 may be made of the same material, and may be formed as a single monolithic piece. In other examples, one or more element may be made of a different material.

The actuator 160, including the head 166, shaft 162, and clamp 164 may be made as a single monolithic piece. In other examples, one or more of the head 166, shaft 162, and clamp 164 may be made of a different material. These materials include, but are not limited to, reinforced nylon, hard plastic such as polyvinylchloride (PVC), high-density polyethylene (HDPE), polystyrene (PS), polycarbonate, acrylonitrile butadiene styrene (ABS), and polypropylene (PP), and metal or metal alloys.

While the different lengths of cannulas provide a good fit to a specific tissue thickness or depth, the clinician needs to determine the tissue thickness or depth before choosing a cannula length. In addition, tissue thicknesses or depths may alter during the surgical procedure, due to patient swelling and extravasation, potentially requiring multiple cannula lengths for the procedure. To more easily accommodate differing and changing tissue depths, a flexible cannula configured to be secured to various tissue thicknesses is desired.

Figure 8:
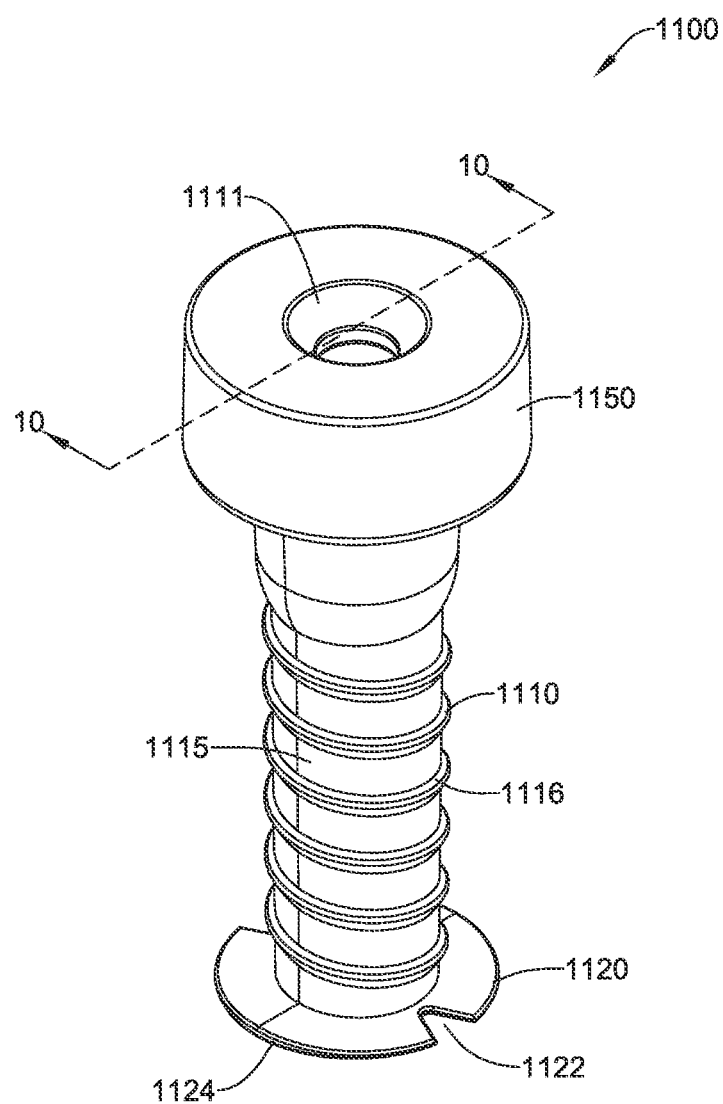
FIG. 8 is a perspective view of another exemplary cannula.

FIG. 8 shows a flexible cannula 1100 with a distal flange 1120 with relief slits or notches 1122 so the distal flange 1120 may be flexed proximally for insertion, which may allow the cannula 1100 to be inserted on an obturator, thus removing the need for a hemostat or other tool external to the cannula 1100. A valve seals the passageway through the cannula 1100 both when an instrument is inserted through the passageway of the cannula 1100 and when no instrument is inserted therein.

The cannula 1100 may include an elongated body 1110 having a shaft 1115 with a longitudinal axis, and a distal flange 1120. The body 1110 may be formed of a flexible polymeric material. The cannula 1100 may include a cap 1150 disposed on the proximal end of the elongated body 1110. The body 1110 defines a passageway or lumen 1111 extending along the longitudinal axis. When inserted into a skin incision, the cap 1150 may sit outside the joint space, on or above the skin, and serve as the entry point for the necessary devices for the procedure. The shaft 1115 may include an exterior structure configured to aid in inserting and retaining the cannula 1100 in the skin incision. In the example shown in FIG. 8, the exterior structure is a helical thread 1116. When the cannula 1100 is screwed into the skin incision, the distal flange 1120 may sit inside the joint space and retract surrounding soft tissue to improve visualization inside the joint space.

The distal flange 1120 may extend radially outward from the distal end of the body 1110. The distal flange 1120 may be generally circular as illustrated, or oval, teardrop, or stadium in shape, and may have similar or different shapes and diameters. The distal flange 1120 may have relief elements so that the flange 1120 may easily bend back and forth between a first, biased radial configuration in which the distal flange 1120 extends radially outward from the body 1110, as shown in FIG. 8, and a second, deflected or folded configuration in which the distal flange 1120 is bent proximally during insertion through a skin incision. It is noted that in some instances, the flange 1120 may be deflected or folded distally during insertion through a skin incision, if desired. The distal flange 1120 is biased in the radial configuration when not subjected to an external force. In one example, the relief elements include a plurality of notches 1122 cut into the outer perimeter 1124 of the distal flange 1120. The notches 1122 may be triangular cuts with the widest part of the cut at the perimeter of the distal flange 1120 and side edges of the notches converging radially inwardly toward the longitudinal axis of the body 1110, as shown in FIG. 8. In other embodiments, the notches 1122 may be circular, oval, or teardrop in shape.

Figure 9:
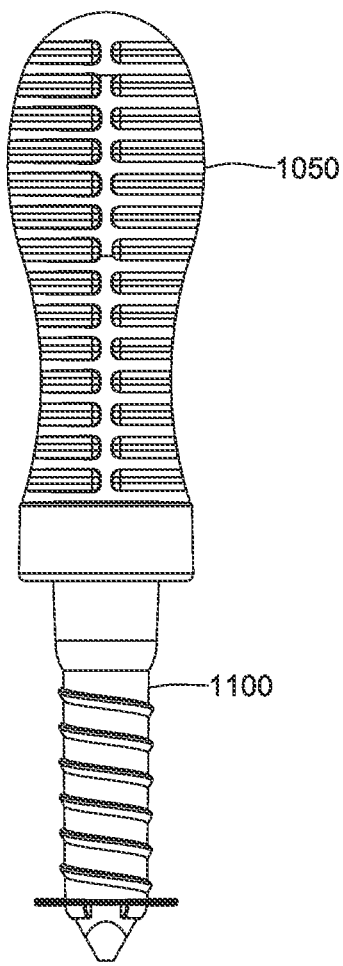
FIG. 9 is a side view of the cannula of FIG. 8 on an obturator.

The cannula 1100 may be inserted using an obturator, extending through the lumen 1111, as shown in FIG. 9. For example, the shaft of the obturator 1050 may be inserted through the passageway or lumen 1111 of the cannula 1100 to provide rigidity when passing the cannula 1100 through a skin incision. The distal tip of the shaft of the obturator 1050 may extend beyond the distal flange 1120 to facilitate insertion through a skin incision.

Figure 10:
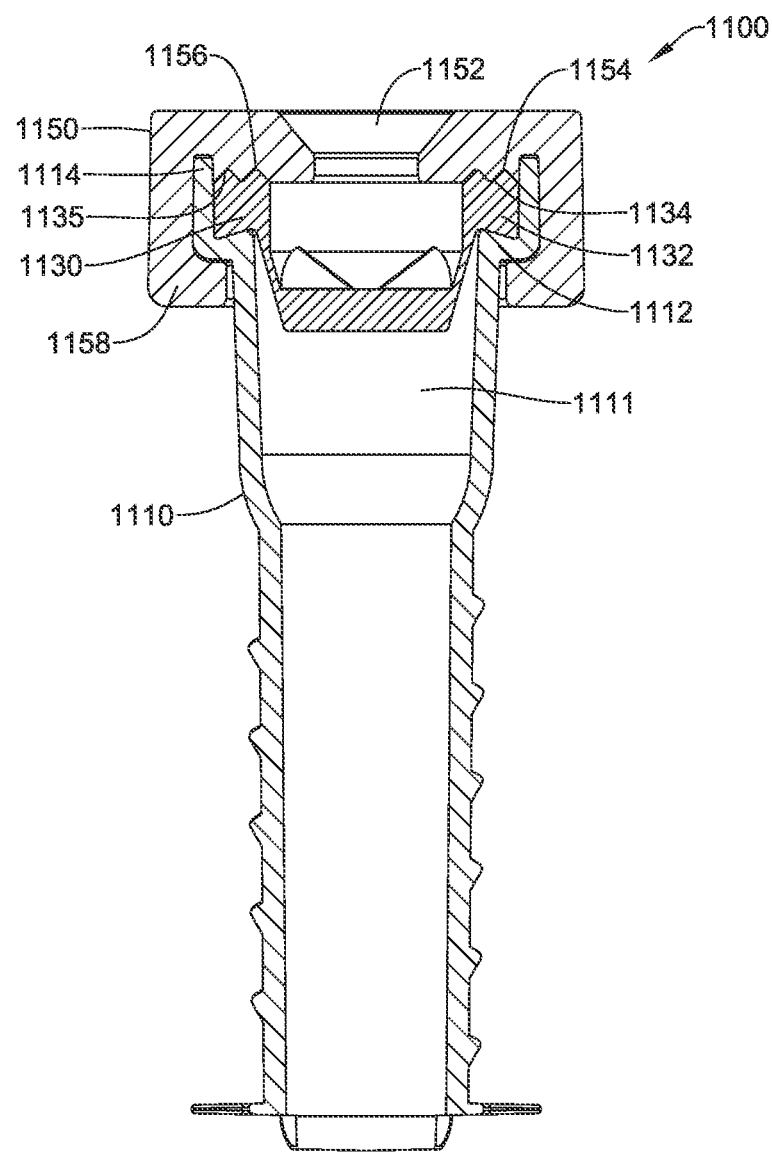
FIG. 10 is a cross-sectional view of the cannula of FIG. 8, taken along line 10-10.

The cannula 1100 illustrated in FIGS. 8-12 may include at least one valve 1130 secured to the body 1110 by a flexible cap 1150. In some instances, the flexible cap 1150 forms a non-compressive seal with the valve 1130. The non-compressive seal is configured to prevent or limit the amount of fluid escaping through the lumen 1111 of the cannula and to maintain the hydrostatic pressure inside the joint space, both when an instrument is inserted through the lumen 1111 and when no instrument is present in the lumen 1111. The valve 1130 may be located within an interior of the body 1110 adjacent the proximal end, as shown in FIG. 10. The body 1110 may have a shoulder 1112 extending radially outward, with a proximally facing surface creating a seat for a circumferential flange 1132 on the valve 1130. In some examples, the shoulder 1112 defines an undercut in which the proximally facing surface of the shoulder 1112 has a downward angle (i.e., is tapered distally in a radially outward direction), and the circumferential flange 1132 may have a mating distally facing surface having a downward angle (i.e., tapering distally in a radially outward direction). The cap 1150 may include a distal flange 1158 configured to engage the shoulder 1112 (e.g., interlock and/or form a snap-fit) to secure the cap 1150 onto the body 1110. The cap 1150 is flexible, i.e., formed of a flexible polymeric material) to allow the distal flange 1158 to flex outward as it moves over the proximal end 1114 of the body 1110, and then return to the biased configuration with the distal flange 1158 positioned under the shoulder 1112 as shown in FIG. 10.

The non-compressive seal may be formed by a tortuous pathway defined between the distally facing inner surface 1154 of the cap 1150 and the proximal surface 1134 of the valve 1130 which interfaces with (i.e., is juxtaposed with) the distally facing inner surface 1154. In some examples, the tortuous pathway is defined by a non-linear proximal surface 1134 on the valve 1130 and a corresponding, complementary non-linear inner surface 1154 on the cap 1150. The proximal surface 1134 of the valve 1130 may have a first mating geometry and the inner surface 1154 of the cap 1150 may have a second mating geometry complementary to the mating geometry of the proximal surface 1134. When the cap 1150 is disposed on the valve 1130 within the body 1110 and the first mating geometry engages the second mating geometry such that the proximal surface 1134 of the valve 1130 is juxtaposed with the inner surface 1154 of the cap 1150, a non-compressive seal is created therebetween. The tortuous pathway created between the inner surface 1154 of the cap 1150 and the proximal surface 1134 of the valve 1130 substantially prevents fluid from escaping from the lumen 1111 in the absence of compressive forces between the cap 1150, valve 1130, and body 1110.

Due to the non-compressive seal created between the cap 1150 and valve 1130, the cap 1150 may be flexible, with a durometer the same as or less than the durometer of the body 1110. In some examples, the cap 1150 may be a polymeric material (e.g., silicone) having a durometer of 80 Shore A or less. In other examples, the cap 1150 may have a durometer of 60 Shore A or less. The cap 1150 may also be elastic, in order to stretch around the valve 1130 and body 1110. In some examples, the cap 1150 may have an elasticity from 100% to 300%, meaning the cap 1150 is formed from a material that can be extended elastically about 100 to 300 percent or more of its original length. The body 1110 may be a polymeric material (e.g., silicone) having a durometer of 80 Shore A or less. In other examples, the body 1110 may have a durometer of 60 Shore A or less. The cap 1150 may include a central opening 1152 configured to allow insertion of an instrument therethrough. Due to the flexible nature of the cap 1150, the peripheral rim of the cap 1150 defining the opening 1152 may function as a secondary valve, sealing around the instrument inserted through the cannula 1100.

The relatively soft and flexible material of the cap 1150 also provides the advantage of ease of assembly in that the cap 1150 may be pushed onto the body 1110 with the distal flange 1158 flexing outward as it moves over the proximal end 1114 of the body 1110, and then returning to the biased configuration with the distal flange 1158 positioned under the shoulder 1112, as shown in FIG. 10. In other examples, the inner surface 1154 may be a surface of a separate flexible ring fixed to a rigid cap 1150.

In one example, the tortuous pathway defining the non-compressive seal involves the first mating geometry on the proximal surface 1134 of the valve having at least one ridge 1135 and the second mating geometry on the inner surface 1154 of the cap 1150 having at least two ridges 1155 separated by a channel 1156 therebetween. When the cap 1150 engages the valve 1130, the at least one ridge 1135 on the valve 1130 is received within the channel 1156 on the cap 1150. In another example, the tortuous pathway defining the non-compressive seal involves the first mating geometry on the proximal surface 1134 of the valve having at least two ridges 1135 separated by a channel therebetween and the second mating geometry on the inner surface 1154 of the cap 1150 having at least one ridge 1155 configured to be disposed in the channel. When the cap 1150 engages the valve 1130, the at least one ridge 1155 on the cap 1150 is received within the channel on the valve 1130. In the example valve 1130 illustrated in FIGS. 11A and 11B, the first mating geometry on the proximal surface 1134 of the valve 1130 includes two circumferential ridges 1135 separated by a channel 1136. The matching second mating geometry on the cap 1150 is illustrated in FIG. 12, and includes first, second, and third ridges 1155 separated by two channels 1156. When the cap 1150 is disposed over the valve 1130 and body 1110, as illustrated in FIG. 10, the two ridges 1135 on the valve 1130 are received within the two channels 1156 on the cap 1150.

Figure 11A:
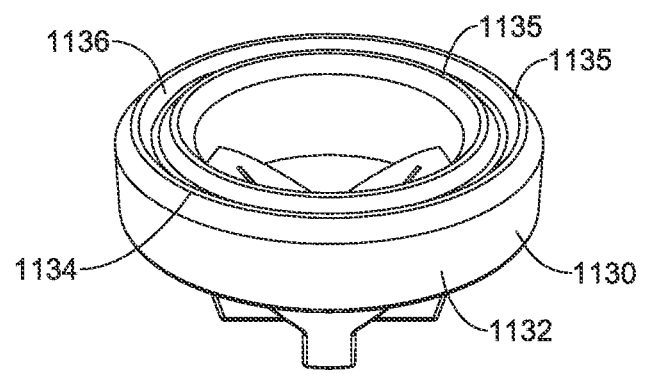
FIGS. 11A and 11B are perspective views of the valve shown in FIG. 10.
Figure 11B:
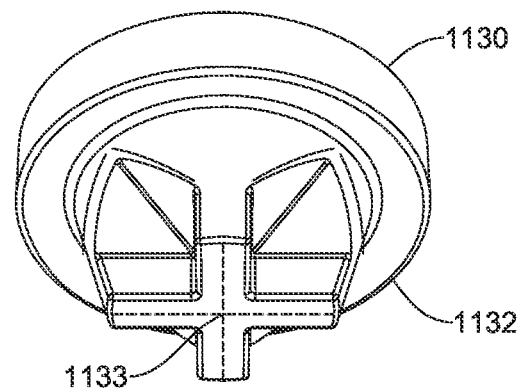
Figure 12:
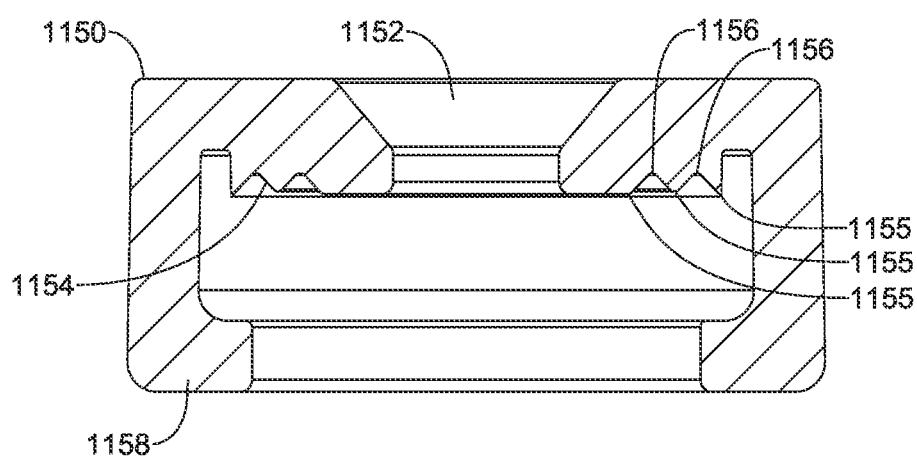
FIG. 12 is an enlarged view of the cap shown in FIG. 10.

The valve 1130 may have an opening such as the cross slit 1133 illustrated in FIG. 11B. In other examples, the opening may be a single slit, tri-slit or may be defined by any number of intersecting slits. The opening will be biased closed in the absence of any instrument disposed through the valve 1130, and will seal around an instrument inserted through the valve 1130.

The cap 1150 may be more flexible than the body 1110, and in some examples, the cap 1150 may also be more flexible than the valve 1130. In some examples, the cap 1150 may be silicone or other flexible material, and may have a Shore A hardness of between 40 and 80. The body 1110 may be silicone or other flexible material, and may have a Shore A hardness of between 40 and 80. The valve 1130 may be made of a flexible material having a Shore A hardness of between 40 and 80. In some examples, the valve 1130 may be made of polyurethane (PU), rubber, neoprene, styrene block co-polymers (SBCs), or other thermoplastic elastomers. In some examples, the valve 1130 may be silicone. In some instances, the body 1110 may be made of the same materials as the valve 1130, if desired.

In some examples, the body 1110 may be cylindrical and may include a surface protrusion or texture that aids in securing the body 1110 within the skin incision. The surface protrusion or texture may further allow the body 1110 to be secured to a variety of depths of skin incision, providing the advantages of not requiring the user to determine the depth of skin incision prior to use, and providing a "one size fits all" body 1110 for use in a variety of depths of skin incision.

Figure 13:
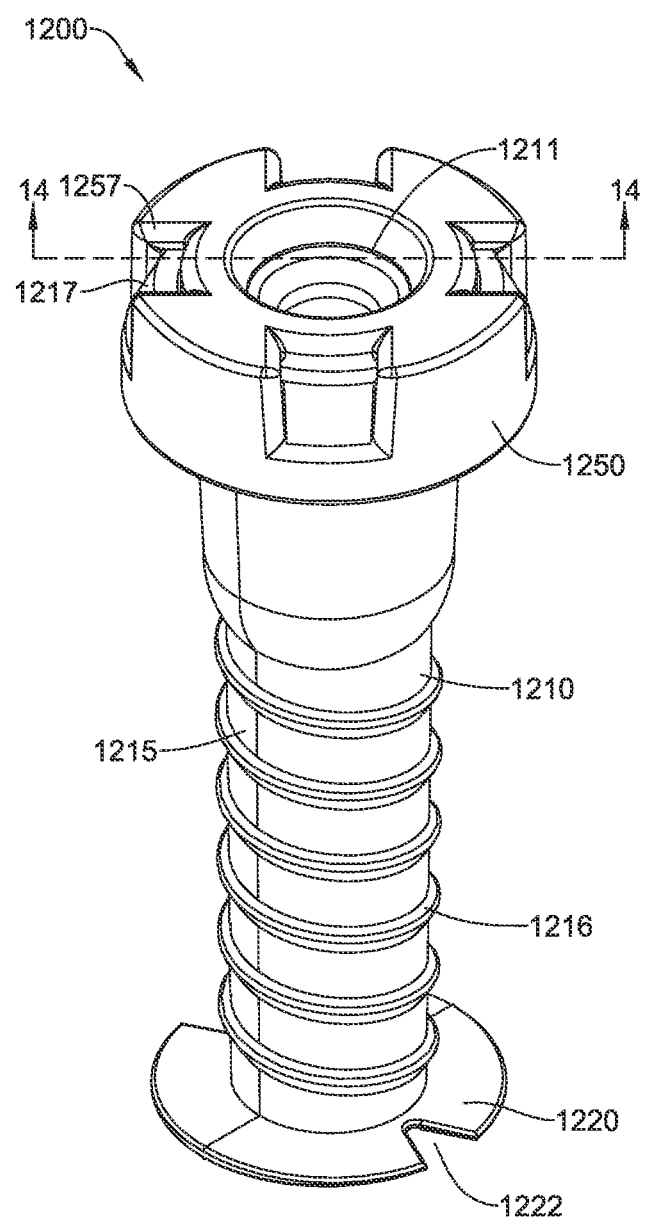
FIG. 13 is a perspective view of a further exemplary cannula.
Figure 14:
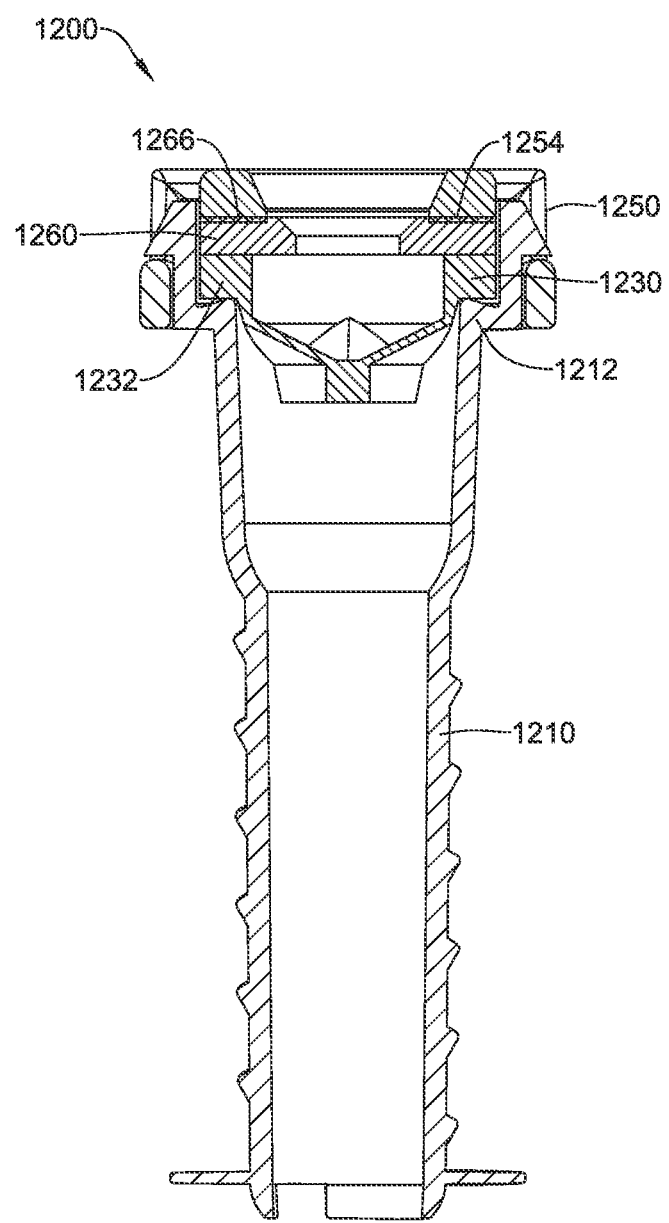
FIG. 14 is a cross-sectional view of the cannula of FIG. 13, taken along line 14-14.
Figure 15:
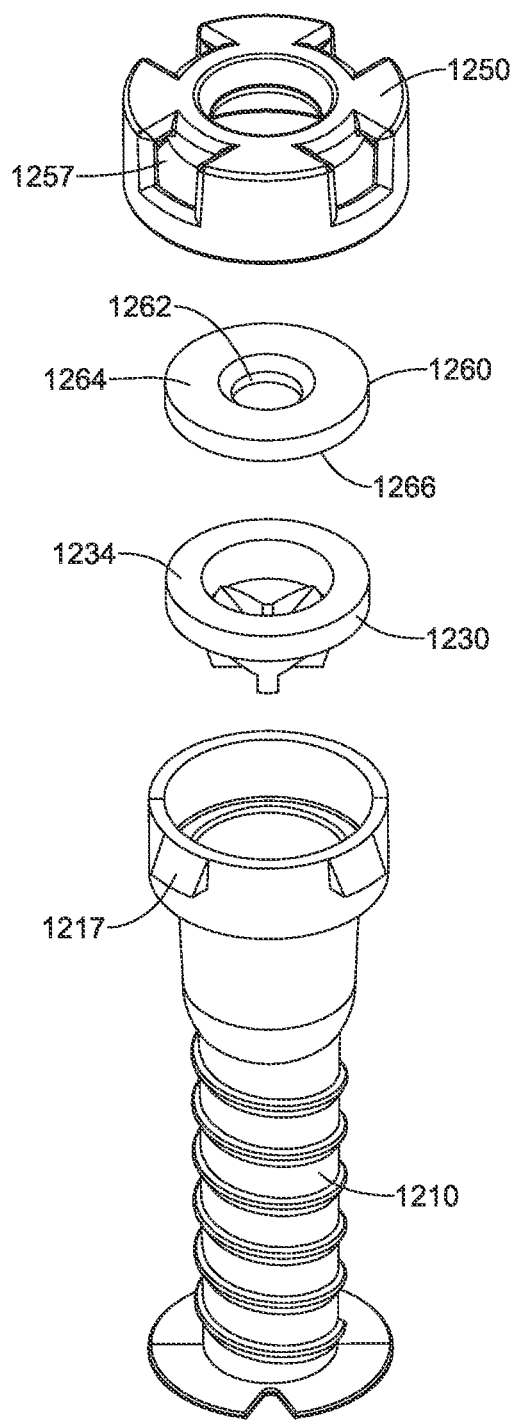
FIG. 15 is an exploded view of the cannula of FIG. 13.

FIGS. 13-15 illustrate another embodiment of a cannula 1200 that includes an elongated body 1210, a first valve 1230, a second valve 1260, and a cap 1250. The elongated body 1210 may be similar to the body 1110 described above, with the added feature of a plurality of tabs 1217 configured to extend through apertures 1257 in the cap 1250 to secure the cap 1250 to the body 1210, as shown in FIG. 13. The body 1210 may have a shaft 1215 with an exterior structure such as a helical thread 1216, and a distal flange 1220 with notches 1222, similar to the body 1110 described above.

The cannula 1200 may include a first valve 1230 and a second valve 1260, and the cap 1250 may be rigid and be connected to the body 1210 in a manner that compresses the first valve 1230 and second valve 1260 between the body 1210 and cap 1250 to form a compression seal. The second valve 1260 may be juxtaposed with a proximal surface of the first valve 1230, in some instances. As shown in FIGS. 14 and 15, the first valve 1230 may be similar to the valve 1130 discussed above, except for having a substantially planar proximal surface 1234. The second valve 1260 may be shaped as a ring with a rim extending around a perimeter of a central opening 1262 configured to seal around an instrument inserted through the central opening 1262 and the passageway of the cannula 1200. The second valve 1260 may have a planar proximal surface 1264 and a planar distal surface 1266. The distally facing inner surface 1254 of the cap 1250 may also be planar. The first valve 1230, second valve 1260, and body 1210 may be made of the materials described above with reference to the valve 1130 and body 1110, above.

The first valve 1230 may be located within the body 1210 adjacent the proximal end, as shown in FIG. 14. The body 1210 may have a shoulder 1212 extending radially outward, with a proximally facing surface creating a seat for a circumferential flange 1232 on the first valve 1230. In some examples, the shoulder 1212 may define an undercut in which the proximally facing surface of the shoulder 1112 has a downward angle (i.e., is tapered distally in a radially outward direction), and the circumferential flange 1232 may have a mating distally facing surface having a downward angle (i.e., tapering distally in a radially outward direction). The second valve 1260 may be placed over the first valve 1230 with the proximal surface 1234 of the first valve 1230 juxtaposed with and engaging the distal surface 1266 of the second valve 1260. The cap 1250 is placed over the second valve 1260 with the proximal surface 1264 of the second valve 1260 engaging the distally facing inner surface 1254 of the cap 1250. The tabs 1217 on the body 1210 extend through apertures 1257 in the cap 1250, thereby securing the cap 1250 to the body 1210 and compressing the first and second valves 1230, 1260 in a compression fit between the cap 1250 and the body 1210.

The valves 1130, 1230, 1260 may be made from a polymer material such as polyisoprene, to substantially reduce the amount of tearing or wear as a result of insertion and/or withdrawal of sharp instruments. The body 1110, 1210 and flexible cap 1150 may also be made of polyisoprene. Other natural or synthetic materials known to one of ordinary skill in the art, and that would substantially reduce the amount of tear or wear, could also be used for any or all of the body 1110, 1210, valves 1130, 1230, 1260, and flexible cap 1150. These materials include, but are not limited to, silicone, rubber, vinyl, polyurethane elastomers, or a combination of components, including styreneethylene-butylene-styrene (SEBS) block co-polymers, polyolefins, mineral oils, and silicone oils. The rigid cap 1250 may be made of materials including, but not limited to, reinforced nylon, hard plastic such as polyvinylchloride (PVC), high-density polyethylene (HDPE), polystyrene (PS), polycarbonate, and polypropylene (PP), and metal or metal alloys. In some embodiments, the cannula 1100, 1200 may include a rotatable member disposed around the elongated body 1110, 1210 and configured to engage the exterior structure on the body 1110, 1210 to secure the cannula to the skin incision. In one example, illustrated in FIGS. 16A and 16B, the rotatable member is a nut 1370 moveable axially and rotatably relative to the body 1310 to secure the cannula to a variety of skin incision depths, providing a 'one-size-fits-all' approach. It is noted that the body 1310 may be representative of the body 1110 of the cannula or the body 1210 of the cannula 1200 described above, and thus the discussion herein regarding the rotatable member (e.g., nut 1370) is applicable to either embodiment described above. Only the body 1310 and nut 1370 are shown in FIGS. 16A-16B, however it will be understood that the cannula will include the cap and one or two valves as discussed above.

Figure 16A:
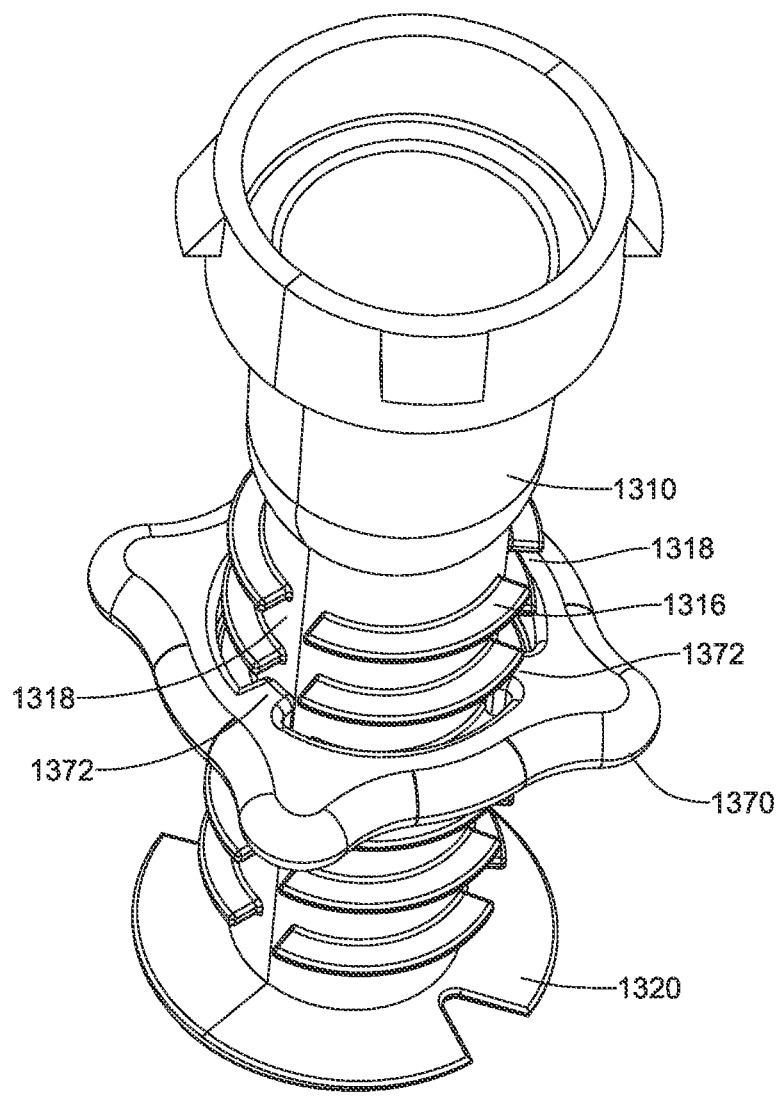
FIG. 16A is a perspective view of an exemplary elongate body of a cannula with a nut disposed thereon in a first position.
Figure 16B:
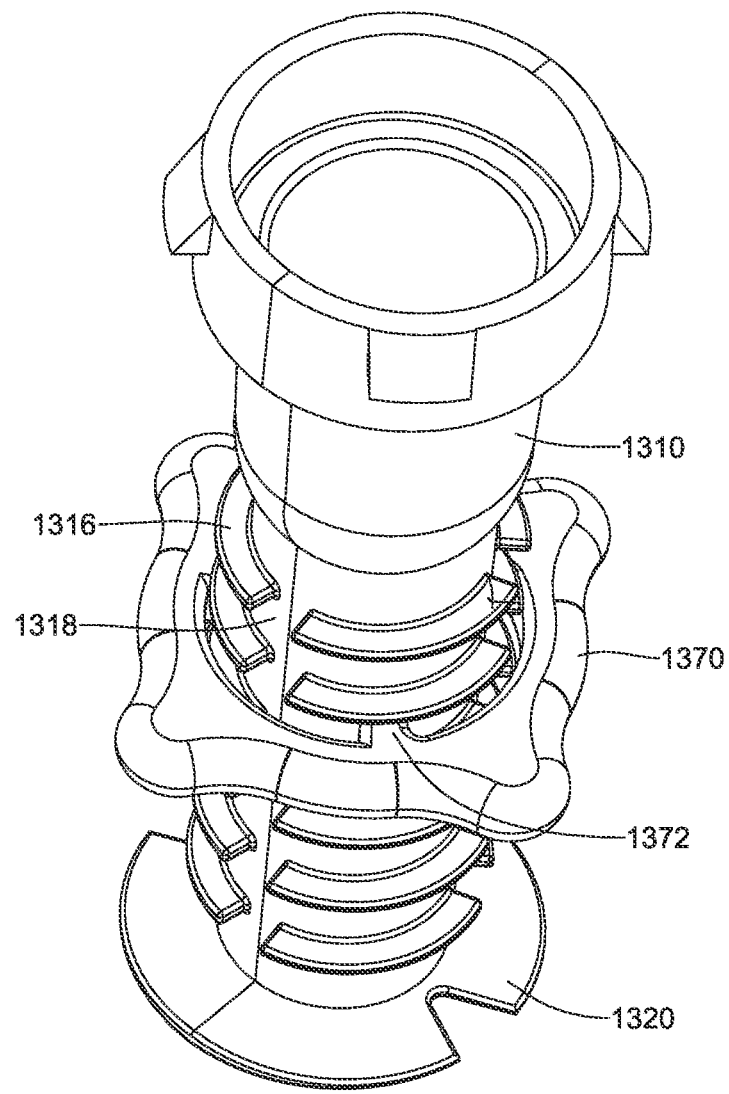
FIG. 16B is a perspective view of the elongate body of a cannula shown in FIG. 16A with the nut disposed thereon in a second position.

In the example illustrated in FIG. 16A, the exterior structure on the elongated body 1310 includes a plurality of circumferential ribs 1316 spaced apart longitudinally along the body 1310. Each rib 1316 is discontinuous (does not extend around the entire circumference of the body 1310) and has a plurality of gaps 1318 between discontinuous segments of each rib 1316, and the gaps 1318 of each rib 1316 are aligned longitudinally along the body 1310 at one or more common circumferential locations. The nut 1370 has a central opening having an inner circumference sized to move over the ribs 1316 (i.e., the radius of the central opening of the nut 1370 is greater than the radial extent of the ribs 1316 from the central longitudinal axis of the body 1310. The nut 1370 may have a plurality of (i.e., two or more) projections 1372 extending inwardly from the inner surface of the nut 1370 into the central opening. The projections 1372 may be rigid and sized and spaced to slide through the gaps 1318, allowing the nut 1370 to slide axially along the body 1310 when the nut 1370 is in the first position shown in FIG. 16A. In other words, the projections 1372 may be arranged at the same angular or circumferential positions as the gaps 1318, such that the projections 1372 can travel longitudinally through the gaps 1318 when rotatably aligned therewith The ability of the nut 1370 to slide axially along the gaps 1318 provides for a rapid insertion and adjustment of the depth of the cannula. This provides an advantage over a conventionally threaded nut and shaft.

For insertion into an incision, the nut 1370 is moved to the proximal end of the body 1310. Once the body 1310 of the cannula is inserted and the flange 1320 is disposed in the joint space, the nut 1370 is rotated to the first position with the projections 1372 rotatably aligned with the gaps 1318 (see FIG. 16A) and the nut 1370 is slid axially distally until the nut 1370 engages the skin. The nut 1370 may then be rotated to a second position, with the projections 1372 between adjacent ribs 1316 and out of rotational alignment with the gaps 1318, as shown in FIG. 16B. The projections 1372 abut the ribs 1316, preventing the nut 1370 from moving axially, keeping the body 1310 in place within the incision. In some examples, the projections 1372 may be sized to contact both the rib 1316 above and the rib 1316 below the projection 1372, providing a friction fit between the ribs 1316 and the projections 1372 as the nut 1370 is rotated. This may prevent the nut 1370 from inadvertently rotating during use until the projections 1372 are in the gap 1318 and allowing the nut 1370 to move axially. The friction fit may be overcome by manually rotating the nut 1370 once the procedure is complete. The adjustable nut 1370 allows the cannula to be used with incisions of varying depth, removing the need for having multiple length cannulas on hand. Further, as tissue thickness can change, and oftentimes expands during procedures, due to general swelling and/or extravasation, the nut 1370 may be rotated to the first position shown in FIG. 16A and slid proximally or distally to accommodate the changing incision depth, and then rotated back to the second position shown in FIG. 16B to secure the cannula. Accordingly, the longitudinal distance between the nut 1370 and the distal flange 1320 can be adjusted as desired to accommodate any thickness of tissue constrained therebetween when the cannula is inserted through a skin incision.

Figure 17A:
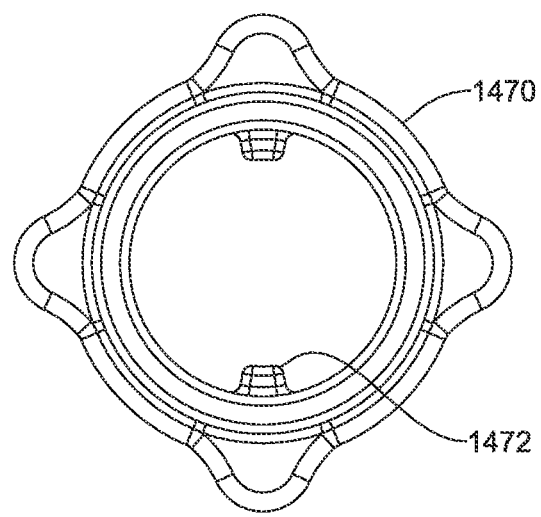
FIGS. 17A and 17B are top views of exemplary nuts with two and three projections, respectively.
Figure 17B:
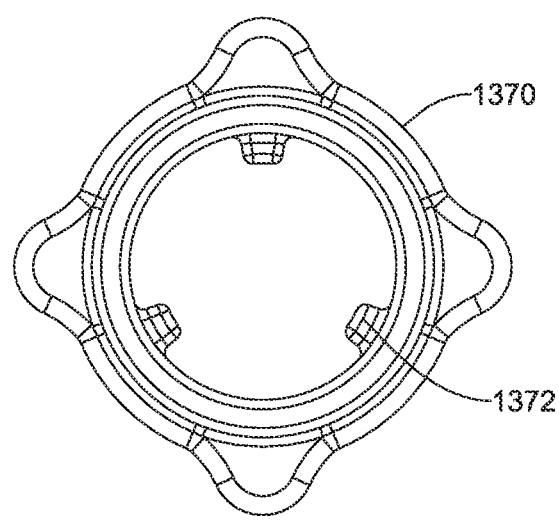

FIGS. 17A and 17B illustrate two embodiments of nut 1470, 1370 with two or three projections 1472, 1372, respectively. It will be understood that the number and/or position of projections 1472, 1372 should correspond with the number and/or position of gaps 1318. The nuts 1470, 1370 may be symmetrically arranged around the circumference of the opening of the nut 1470, 1370. As shown in FIG. 17A, a nut 1470 with two projections 1472 may be configured such that the projections 1472 are positioned 180 degrees apart. As shown in FIG. 17B, a nut 1370 with three projections 1372 may be configured such that the projections 1372 are positioned 120 degrees apart. A nut with four projections may have its projections positioned 90 degrees apart.

Figure 18:
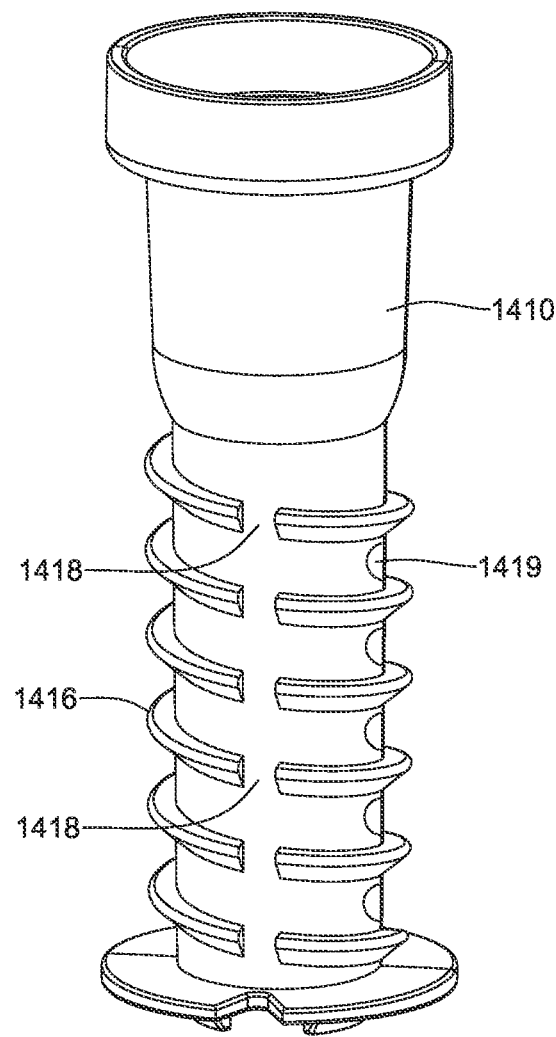
FIG. 18 is a perspective view of an exemplary elongate body with external threading.

In some examples, the surface protrusion or texture on the body that engages the nut may be helical threading. FIG. 18 illustrates an elongated body 1410 of a cannula (valve(s) and cap not shown) with discontinuous threads 1416 interrupted by a series of gaps 1418 aligned longitudinally along the body 1410. In other words, the elongated body 1410 may include discontinuous helical threading with gaps 1418 between discontinuous segments of the helical threading. Each segment of the threading may extend less than 360 degrees, or less than 180 degrees around the circumference of the body 1410, for example. The gaps 1418 may be aligned longitudinally along the body 1410 at one or more common circumferential locations. In this embodiment the body 1410 has a plurality of stops to limit rotation of the nut (not shown). As illustrated, the stops are detents or recesses 1419 in the outer surface of the body 1410. The recesses 1419 are sized and shaped to receive a portion of the projections 1372, 1472 on the nut 1370, 1470. When the nut 1370, 1470 is rotated, the projections 1372, 1472 may engage the outer surface of the body 1410 in a tight fit that allows for rotation. When the projections 1372, 1472 are rotated into the recesses 1419, a portion of the projections 1372, 1472 is received within the recesses 1419, preventing further rotation until a greater rotational force is applied to the nut 1370, 1470.

Figure 19:
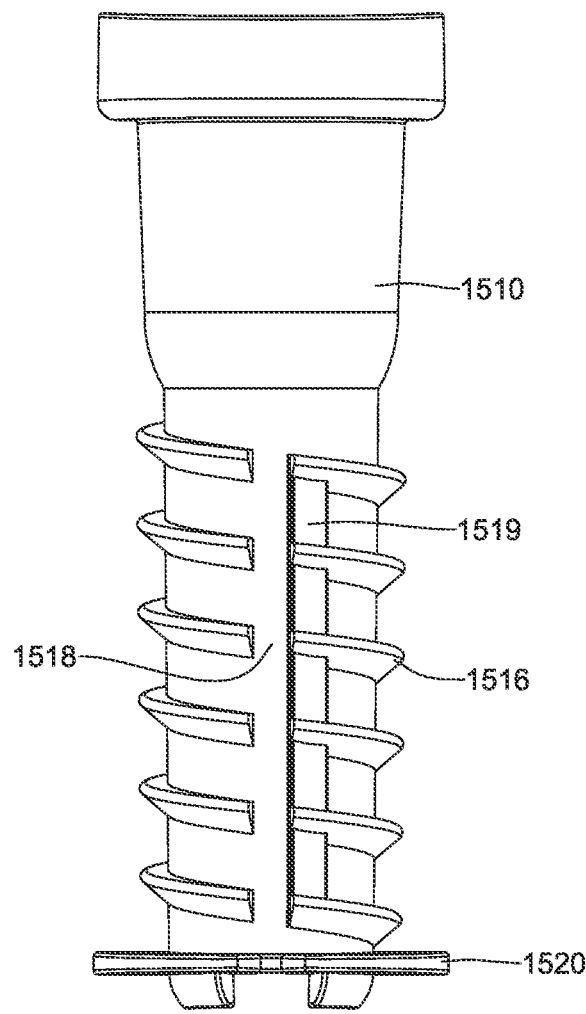
FIG. 19 is a side view of an exemplary elongate body with external threading and stops.

In another example, the stop limiting rotation of the nut 1370, 1470 may be an outwardly extending protrusion 1519 on the outer surface of the body 1510. In the example illustrated in FIG. 19, the body 1510 of the cannula has a discontinuous helical thread 1516 with a plurality of circumferentially aligned gaps 1518 and a plurality of protrusions 1519 positioned adjacent the gaps 1518. The protrusions 1519 may be provided on the distal side of each thread segment, with the thread segment extending helically from the protrusion 1519 toward the distal flange 1520 at the distal end of the body 1510. When the nut 1370, 1470 (not shown) is moved axially down the body 1510 into position against the skin and then rotated, the protrusions 1519 limit the movement of the nut 1370, 1470 when the projections 1372, 1472 of the nut 1370, 1470 abut the protrusions 1519, helping to maintain the nut 1370, 1470 in position to secure the cannula in the incision. The flange 1520 is illustrated as a substantially planar structure with flat distal and proximal surfaces.

Figure 20A:
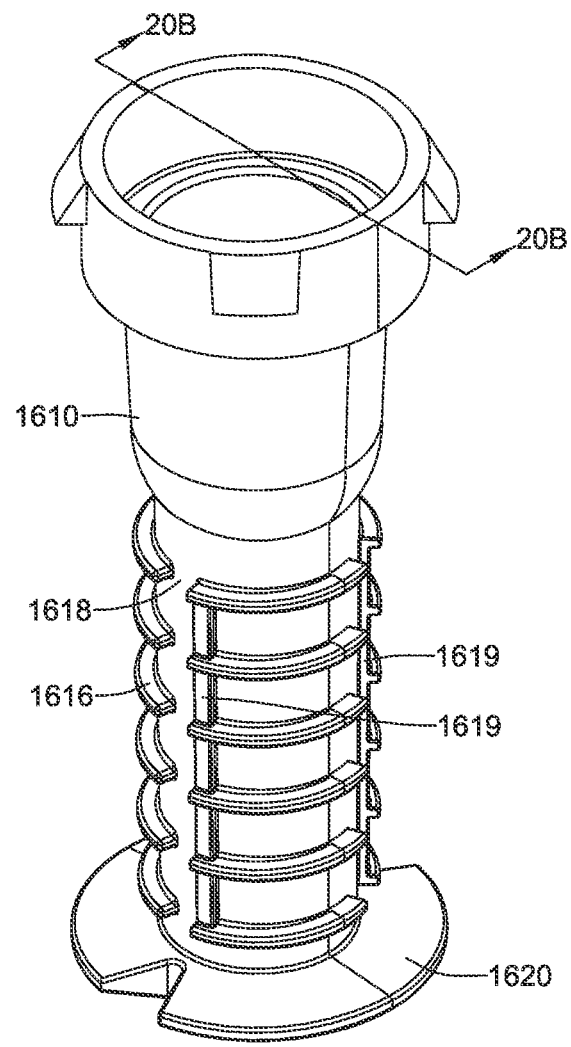
FIG. 20A is a perspective view of another exemplary elongate body with external ribs and stops.
Figure 20B:
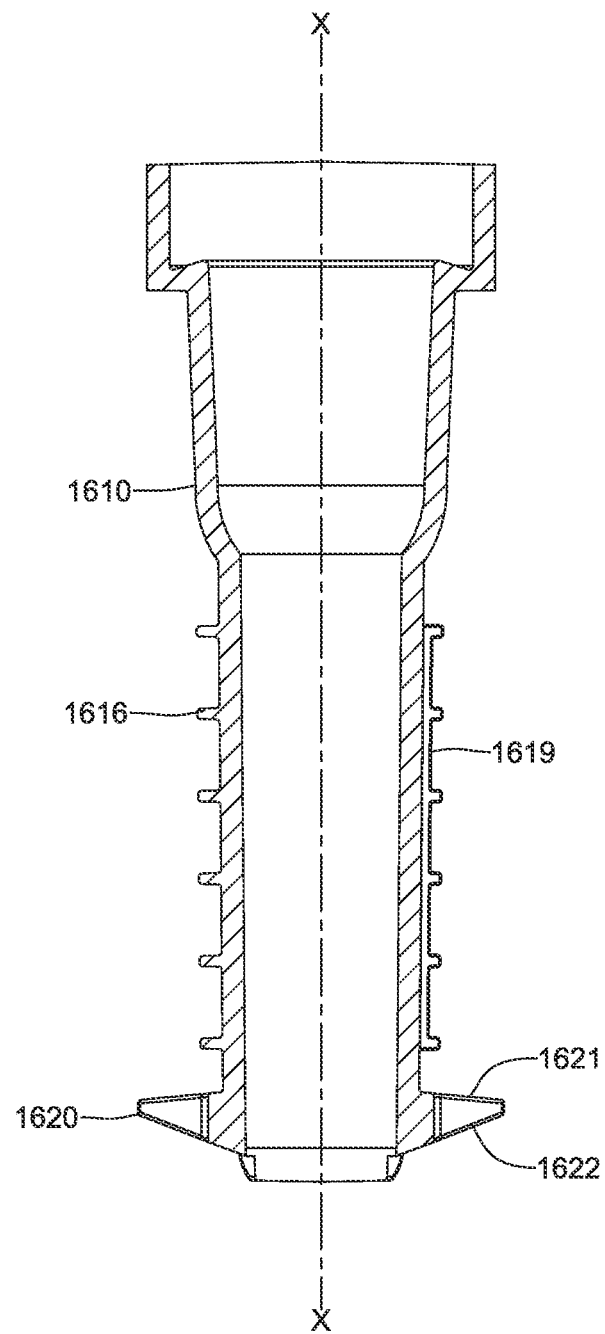
FIG. 20B is a cross-sectional view of the elongate body of FIG. 20A, taken along line 20B-20B.

In the example illustrated in FIGS. 20A and 20B, the body 1610 of the cannula (valve(s) and cap not shown) has a plurality of longitudinally spaced apart discontinuous ribs 1616. Each rib 1616 has a plurality of circumferentially aligned gaps 1618 with a protrusion 1619 adjacent each gap 1618. Similar to the protrusions 1519 on the helical thread 1516 shown in FIG. 19, the protrusions 1619 limit the rotation of the nut 1370, 1470 and help secure the cannula, preventing the nut 1370, 1470 from accidental rotation into the adjacent gap 1618. As shown in the cross-sectional view in FIG. 20B, the ribs 1616 are rectangular, with proximal and distal surfaces substantially perpendicular to the longitudinal axis x-x of the body 1610. The flange 1620 is wedge shaped in cross-section, with a proximal surface 1621 substantially perpendicular to the longitudinal axis x-x and a distal surface 1622 angled proximally as it extends from the body 1610. The wedge shaped flange 1620 may aid in keeping the cannula in place in the incision, preventing the flange 1620 from being bent distally, while allowing for the flange 1620 to be bent proximally during insertion.

Figure 21A:
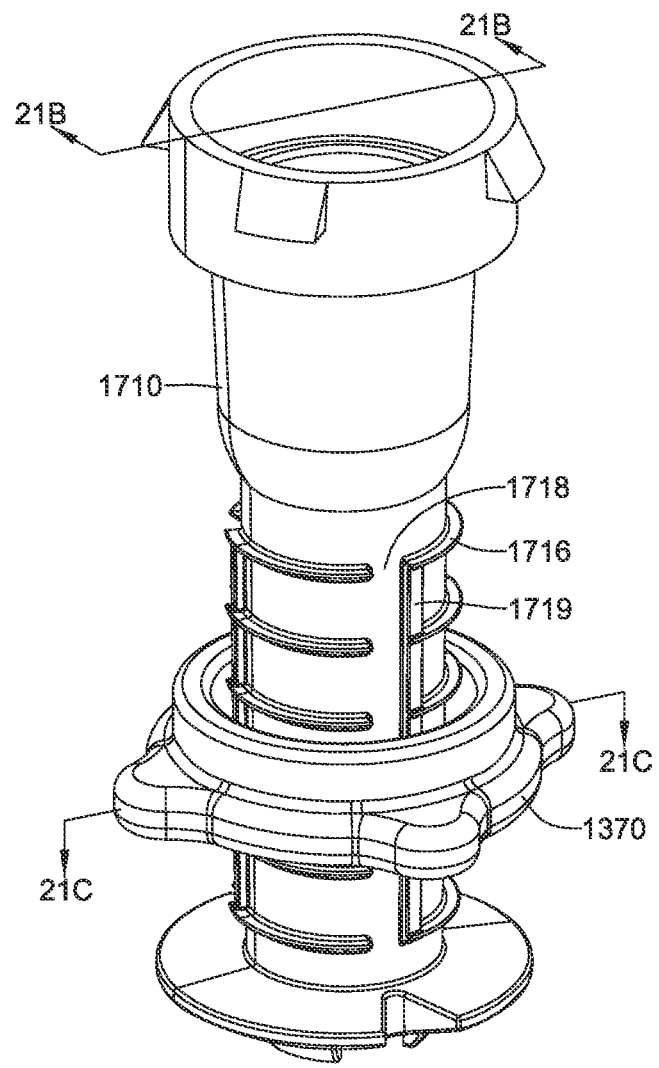
FIG. 21A is a perspective view of another exemplary elongate body of a cannula with external angled ribs and stops with a nut disposed thereon.
Figure 21B:
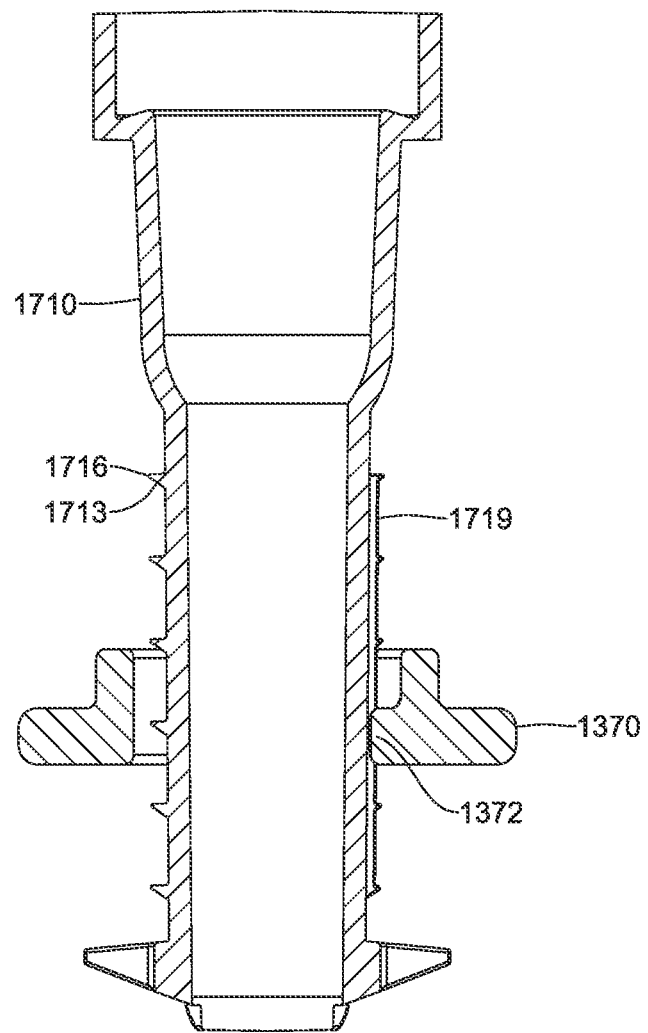
FIG. 21B is a cross-sectional view of the elongate body of FIG. 21A, taken along line 21B-21B.
Figure 21C:
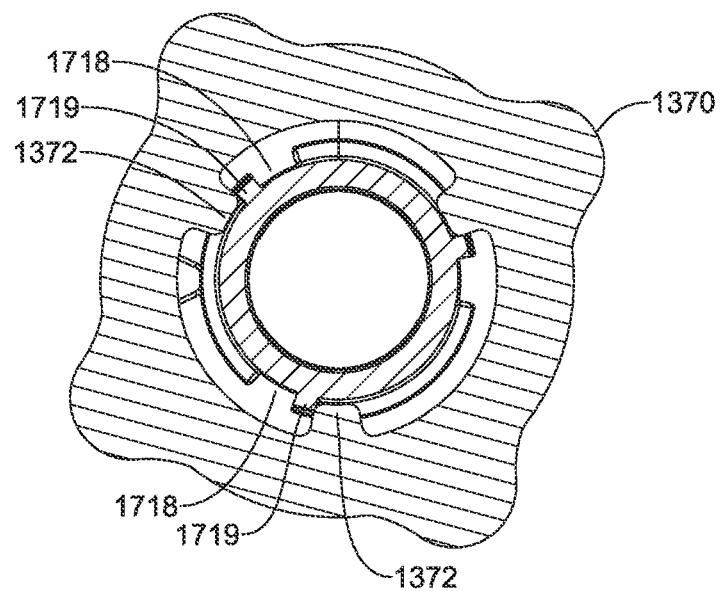
FIG. 21C is a cross-sectional view of the elongate body of FIG. 21A, taken along line 21C-21C.

FIGS. 21A, 21B, and 21C illustrate a body 1710 of a cannula (valve(s) and cap not shown) with the nut 1370 in place. The body 1710 as illustrated is similar to the body 1610 shown in FIGS. 20A and 20B, but the ribs 1716 are wedge shaped and have angled distal surfaces 1713, as shown in FIG. 21B. FIG. 21C shows the projections 1372 on the nut 1370 abutting the protrusions 1719 adjacent each gap 1718.

Figure 22A:
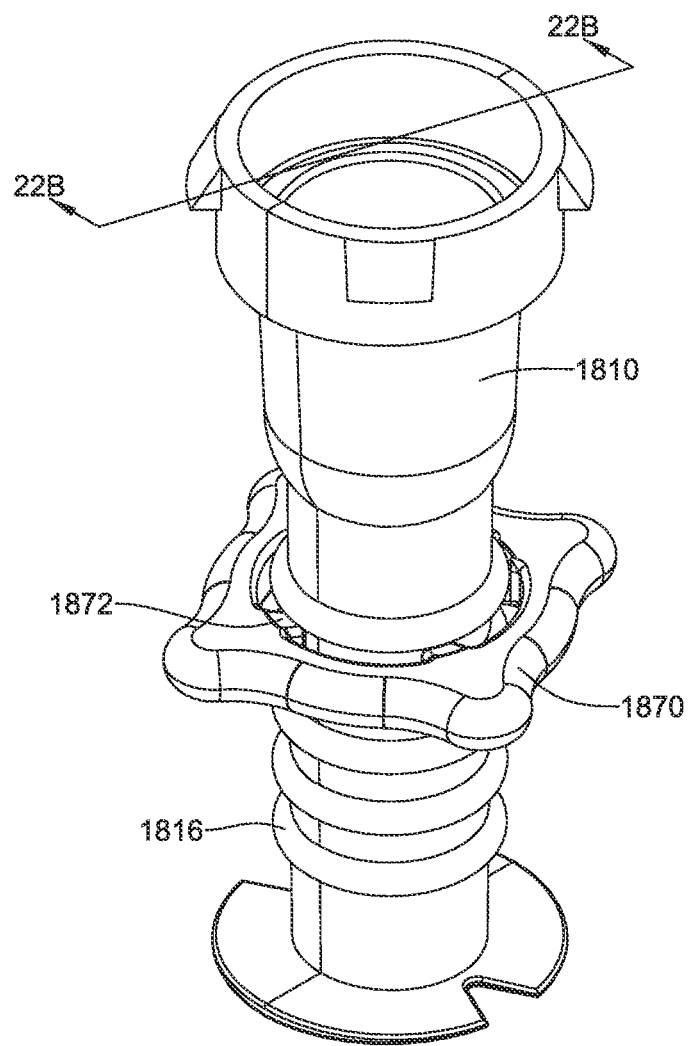
FIG. 22A is a perspective view of another exemplary elongate body of a cannula with external rounded circumferential ribs with a nut disposed thereon.
Figure 22B:
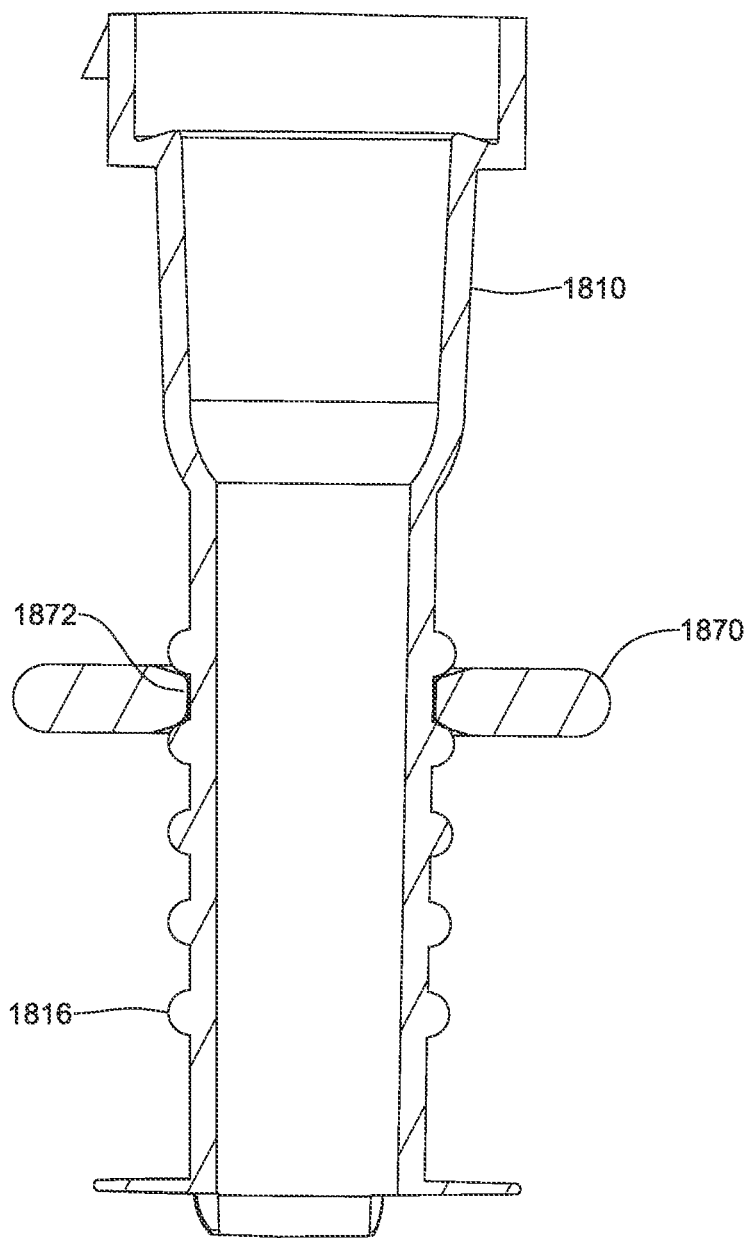
FIG. 22B is a cross-sectional view of the elongate body of FIG. 22A, taken along line 22B-22B.

FIGS. 22A and 22B illustrate a body 1810 of a cannula (valve(s) and cap not shown) with a nut 1870 in place. The nut 1870 is similar to the nut 1370 described above, and has a plurality of projections 1872 extending inward. The body 1810 as illustrated is similar to the bodies 1610 and 1710, but the longitudinally spaced apart ribs 1816 are rounded and extend entirely (e.g., continuously) circumferentially around the body 1810 with no gaps. FIG. 22B shows the projections 1872 on the nut 1870 disposed in the space between adjacent but longitudinally spaced apart ribs 1816. The nut 1870 and projections 1872 may be made of a material that is more rigid than the body 1810 such that when the nut 1870 is moved longitudinally, the body 1810 flexes inward, allowing the projections 1872 on the nut 1870 to move over the ribs 1816. In other examples, the projections 1872 may be more flexible than the body 1810 such that the projections 1872 flex upwards or downwards as the nut 1870 moves longitudinally over the ribs 1816. In some examples, the projections 1872 may be sized to contact both the rib 1816 above and the rib 1816 below the projection 1872 simultaneously, providing a friction fit between the ribs 1816 and the projections 1872 as the nut 1870 is rotated, as discussed above.

There are existing elastomeric valves that serve as components of surgical access devices, such as trocars and cannulas in minimally invasive procedures. Some such valves include duckbill valves, cross-slit valves, and dome valves. The common characteristics between all of these valves are that they are passive, normally closed valves that create a fluid seal when oriented in a specific configuration, as fluid pressure forces the valve closed. In surgical access devices, these valves are used to prevent fluid (gas or liquid) from leaking through surgical portals created via a skin incision. A shortcoming of conventional valves arises when a medical instrument is inserted through the valve, as an opening is created by the surgical instrument disrupting the seal of the valve and permitting fluid to leak past the interface between the surgical instrument and the valve. Due to this leakage, these elastomeric valves are generally combined with a secondary valve that creates a seal around the medical instrument. This two-stage valve design is present in many arthroscopic and laparoscopic trocars and cannulas.

The duckbill valve 2100 shown in FIGS. 23-29, which may be incorporated into a surgical access device, solves the leakage problem and prevents loss of distention fluid while allowing medical instruments to enter the surgical access devices as needed. The valve 2100 may be made of an elastomeric material such as silicone or polyurethane, and has a geometry that creates a fluid seal both with and without a medical instrument inserted through the valve 2100. The geometry includes an arcuate cutout 2180 sized to accommodate the medical instrument to be inserted through the valve 2100. The arcuate cutout 2180 allows the valve 2100 to create a fluid seal around the perimeter of a medical instrument passed therethrough, as well as providing a fluid seal without the medical instrument present, removing the need for a two-stage valve system commonly required to achieve a satisfactory seal.

The valve 2100 may be a duckbill valve including a body member 2105 having a base 2110 and first and second opposing walls 2120, 2130 extending from the base 2110. See FIGS. 23-24B. In some examples, the body member 2105 may include a flange 2102 extending radially outward from the base 2110 beyond the perimeter of the base 2110. The flange 2102 may be sized and configured to be coupled with a cannula. The flange 2102 may extend circumferentially around the base 2110. In other examples, the flange 2102 may extend only partially around the base 2110.

Figure 23:
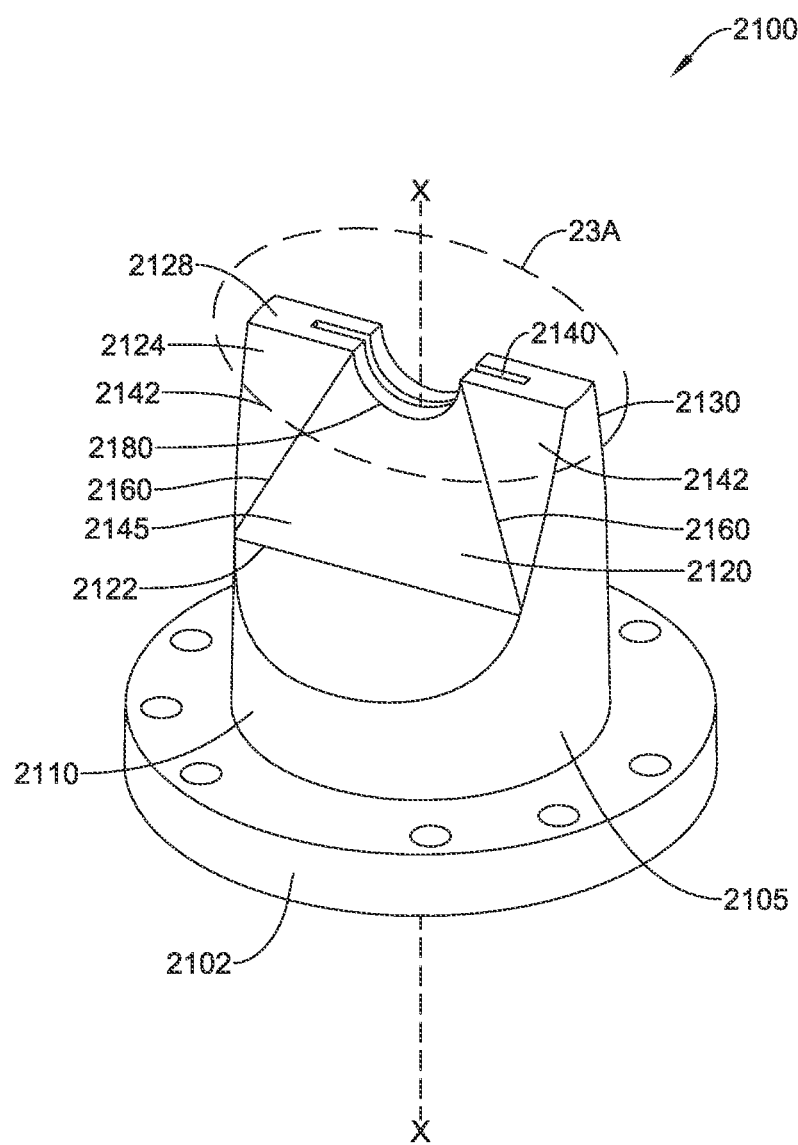
FIG. 23 is a perspective view of an exemplary valve.

The first and second walls 2120, 2130 may be mirror images of one another. The first and second walls 2120, 2130 may have first ends 2122, 2132 spaced apart at the base 2110 and second ends 2124, 2134 converging at a lower surface 2128 of the valve 2100. In some examples, the lower surface 2128 may be substantially perpendicular to the central axis x-x, as shown in FIG. 23. The arcuate cutout 2180 may be provided at the second ends 2124, 2134 of the first and second walls 2120, 2130. The arcuate cutout 2180 may be centered on the central axis x-x of the body member 2105, as shown in FIG. 23. The first and second walls 2120, 2130 may each define a plurality of planes. In the example shown in FIG. 23, each wall 2120, 2130 has side planes 2142 and a center plane 2145. The side planes 2142 may extend from the lower surface toward the base 2110 at a different angle than the center plane 2145.

Figure 24A:
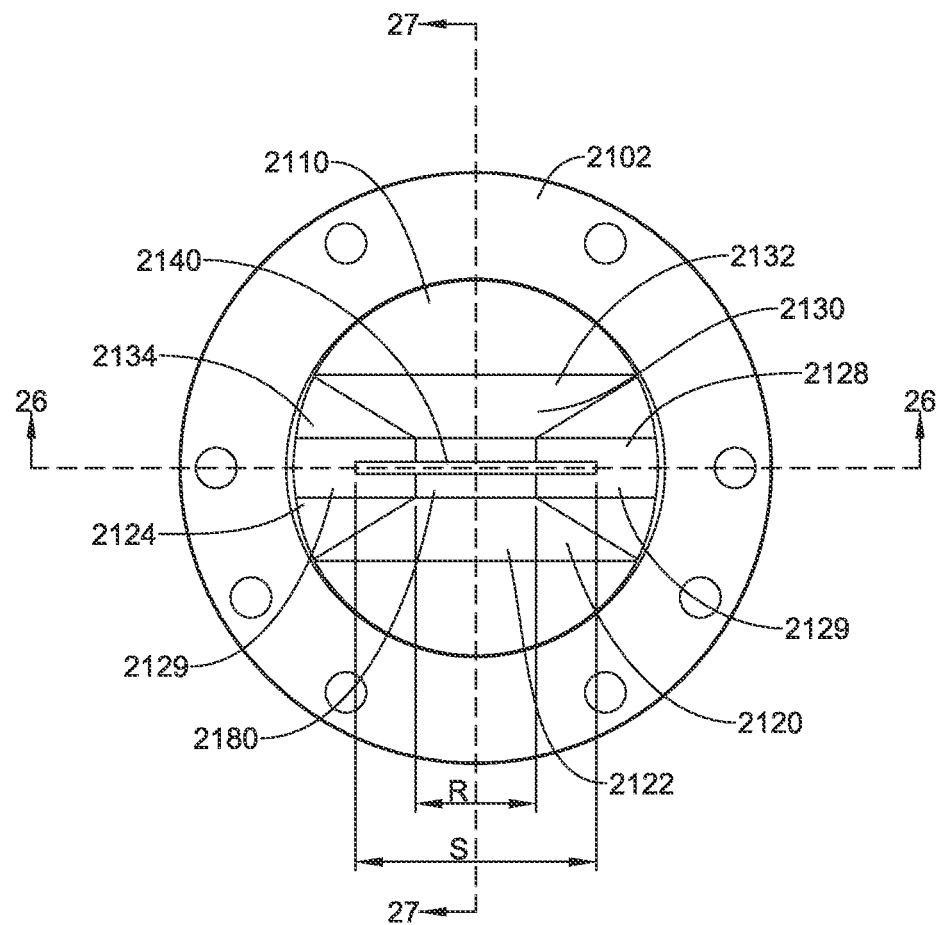
FIG. 24A is an end view of the valve of FIG. 23.

The lower surface 2128 may include a slit 2140 extending at least partially along the length of the lower surface 2128. In some examples, the length S of the slit 2140 (measured perpendicular to the central axis x-x) may be less than the length L of the lower surface 2128 (measured perpendicular to the central axis x-x), as shown in FIG. 24A. The length S of the slit 2140 is measured linearly across the lower surface 2128. In the example shown in FIG. 24A, the length S of the slit 2140 is greater than the length R of the arcuate cutout 2180 (measured perpendicular to the central axis x-s), with the slit 2140 extending laterally beyond the arcuate cutout 2180 but not completely across the lower surface 2128. Thus, the slit 2140 may have a length S greater than the length R of the arcuate cutout 2180, but less than the length L of the lower surface 2128 of the valve 2100.

Figure 24B:
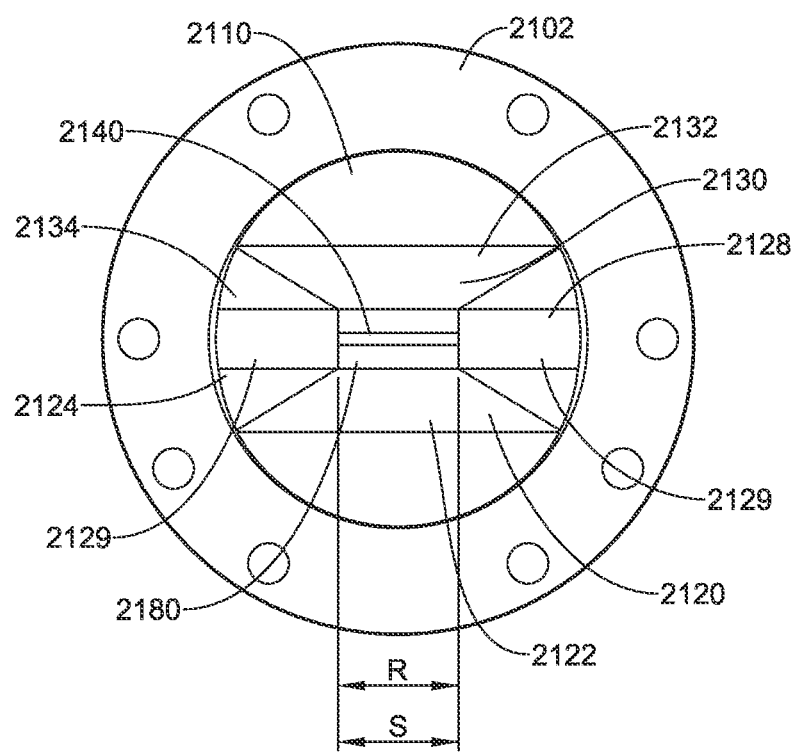
FIG. 24B is an end view of another exemplary valve.

The arcuate cutout 2180, which may be centered along the lower surface 2128, divides the lower surface 2128 into first and second sections 2129 positioned on opposite lateral sides of the arcuate cutout 2180. In some instances, the slit 2140 may extend to about the midpoint of each section 2129, as shown in FIG. 24A. In other examples, the length of the slit 2140 may be equal to or less than the length R of the arcuate cutout 2180 (e.g., equal to or less than the diameter of the arcuate cutout 2180). For example the length S of the slit 2140 is shown to be equal to the length R of the arcuate cutout 2180 (e.g., equal to the diameter of the arcuate cutout 2180), as shown in FIG. 24B. The slit 2140 may have a length of between 0.1 inches and 0.8 inches, between 0.3 inches and 0.5 inches, between 0.2 inches and 0.4 inches, about 0.2 inches, about 0.3 inches, or about 0.4 inches, for example. In one example, the slit has a length of 0.4 inches. The slit 2140 may have a width or thickness of 0.03 inches or less, such as between 0.01 inches and 0.03 inches, or between 0.00 inches and 0.03 inches, for example. A slit having a width or thickness of 0.00 inches refers to an embodiment in which a slit is formed, but due to the nature of the elastic properties of the valve 2100 the walls 2120, 2130 on either side of the slit collapse against one another effectively removing any gap therebetween. Thus while there is a slit, it has a width or thickness of 0.00 inches when the walls 2120, 2130 are in direct contact with one another. Similarly, when no instrument is inserted through the valve 2100, fluid exerts radial pressure on the outside of the walls 2120, 2130, forcing the second ends 2124, 2134 together and closing the slit 2140 thereby preventing fluid from egressing through the valve 2100.

Upon insertion of an instrument through the valve 2100, the slit 2140 expands and the edge of the arcuate cutout 2180 seals around the perimeter of the instrument, allowing the second ends 2124, 2134 of the walls to pinch closed on either side of the arcuate cutout 2180 even though the slit 2140 is longer than the length of the arcuate cutout 2180. Thus, the valve 2100 maintains a fluid seal around the medical device inserted therethrough.

Figure 25A:
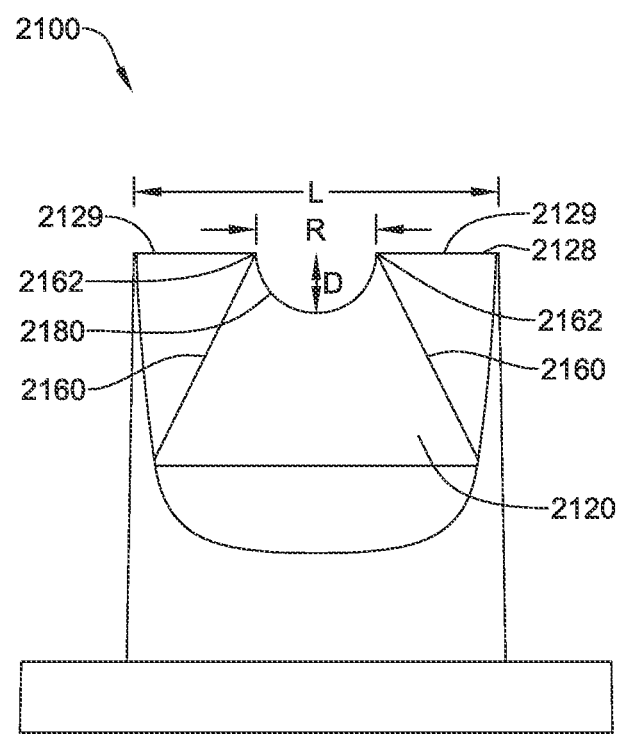
FIG. 25A is a side view of the valve of FIG. 23.

The length R of the arcuate cutout 2180, which in some instances may be a diameter of the arcuate cutout 2180, may be less than the length L of the lower surface 2128. In some instances, the length R of the arcuate cutout 2180, which in some instances may be a diameter of the arcuate cutout 2180, may be less than one-half the length L of the lower surface 2128. In some instances, the radius of the arcuate cutout 2180 may be less than one-half the length L of the lower surface 2128, as shown in FIG. 25A. In some examples, the length L of the lower surface 2128 may be between 0.5 inches and 1.0 inch and the length R may be between 0.1 inches and 0.4 inches. In one example, the length L is 0.6 inches and the length R is 0.2 inches, while the length of the slit 2140 is 0.4 inches. Thus, the slit 2140, which may have a length greater than the length R of the cutout 2180, may extend about 0.1 inches beyond each end of the cutout 2180 in this example. The length S of the slit 2140 may be 4 times or less than the radius of the arcuate cutout 2180, in some examples. In some instances, the length S of the slit 2140 may be less than or equal to twice the radius of the arcuate cutout 2180.

Figure 25B:
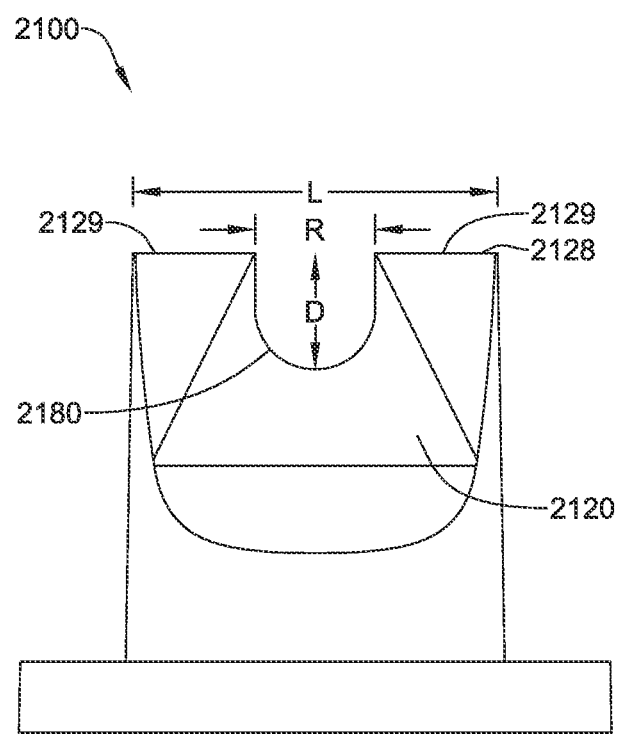
FIG. 25B is a side view of a variation of the valve of FIG. 23.

In some examples, the arcuate cutout 2180 may define a semi-circle, with the depth D being equal to the radius, and thus equal to one-half of the length R, as shown in FIG. 25A. In one example, the radius of a semi-circular arcuate cutout 2180 is 0.1 inches. The length R of the arcuate cutout 2180 may be matched to the diameter of the instrument to be inserted through the valve 2100. The length R of the arcuate cutout 2180 may generally be slightly larger than the diameter of the instrument to be inserted through the valve 2100, but still provide a good seal around the instrument. In some examples, the length R of the arcuate cutout 2180 may be no more than 0.02 inches larger than the diameter of the instrument to be inserted through the valve 2100, or no more than 0.05 inches larger than the diameter of the instrument to be inserted through the valve 2100. In other examples the arcuate cutout 2180 may be U-shaped, with the depth D of the arcuate cutout 2180 being greater than the radius of the arcuate cutout 2180 and/or the length R of the arcuate cutout 2180, as shown in FIG. 25B. For example, the depth D may be between 0.15 inches and 0.45 inches, in some instances.

Figure 23A:
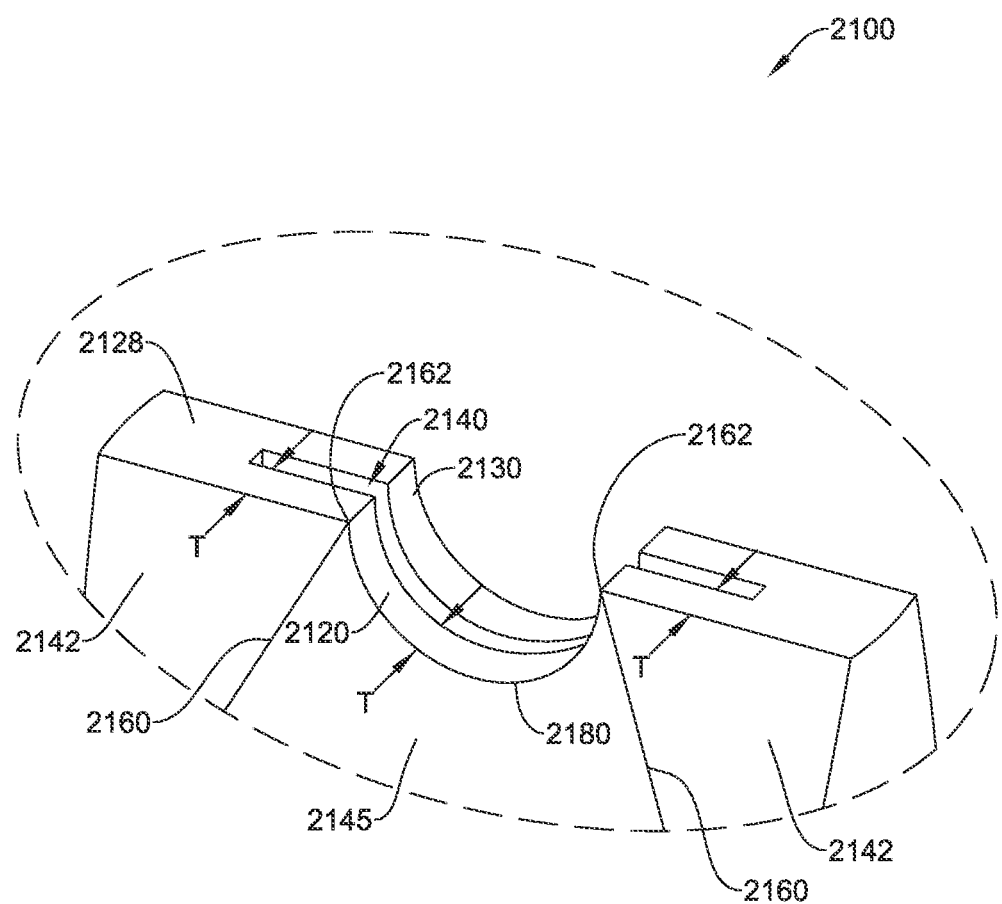
FIG. 23A is an enlarged perspective view of a portion of the valve of FIG. 23.

Referring to FIG. 24A, the center plane 2145 of each wall 2120, 2130 may include converging edges 2160 where the center plane 2145 intersects the side planes 2142. The edges 2160 may extend to a corner 2162 where the arcuate cutout 2180 intersects the lower surface 2128 of the valve 2100. The center plane 2145 may be oriented at an oblique angle to the central axis x-x extending through the valve 2100. Accordingly, the thickness T at the lower end surface 2128 of each of the first and second walls 2120, 2130 may be constant along the entire length of the slit 2140. See FIG. 23A. In other words, the lower end surface 2128 of each of the first and second walls 2120, 2130 may have a constant wall thickness T from the first end of the slit 2140, along the lower end surface 2128 of a first section 2129, along the arcuate cutout 2180, along the lower end surface 2128 of a second section 2129, to the second end of the slit 2140.

Figure 26:
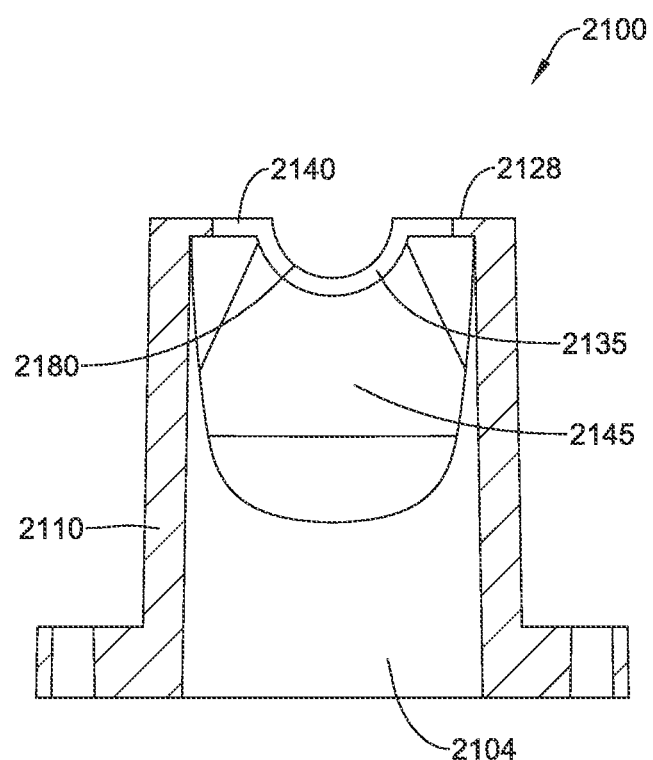
FIG. 26 is a cross-sectional view of the valve of FIG. 24A taken along line 26-26.
Figure 27:
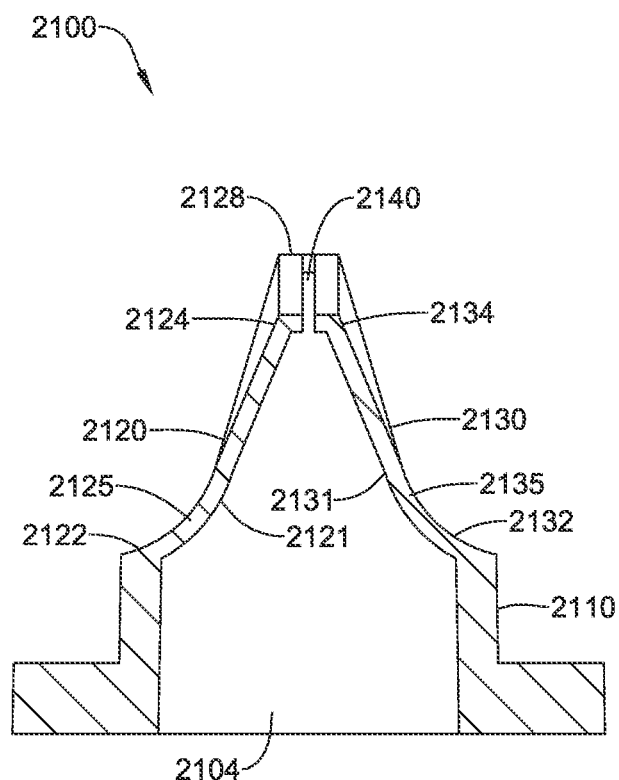
FIG. 27 is a cross-sectional view of the valve of FIG. 24A taken along line 27-27.
Figure 28:
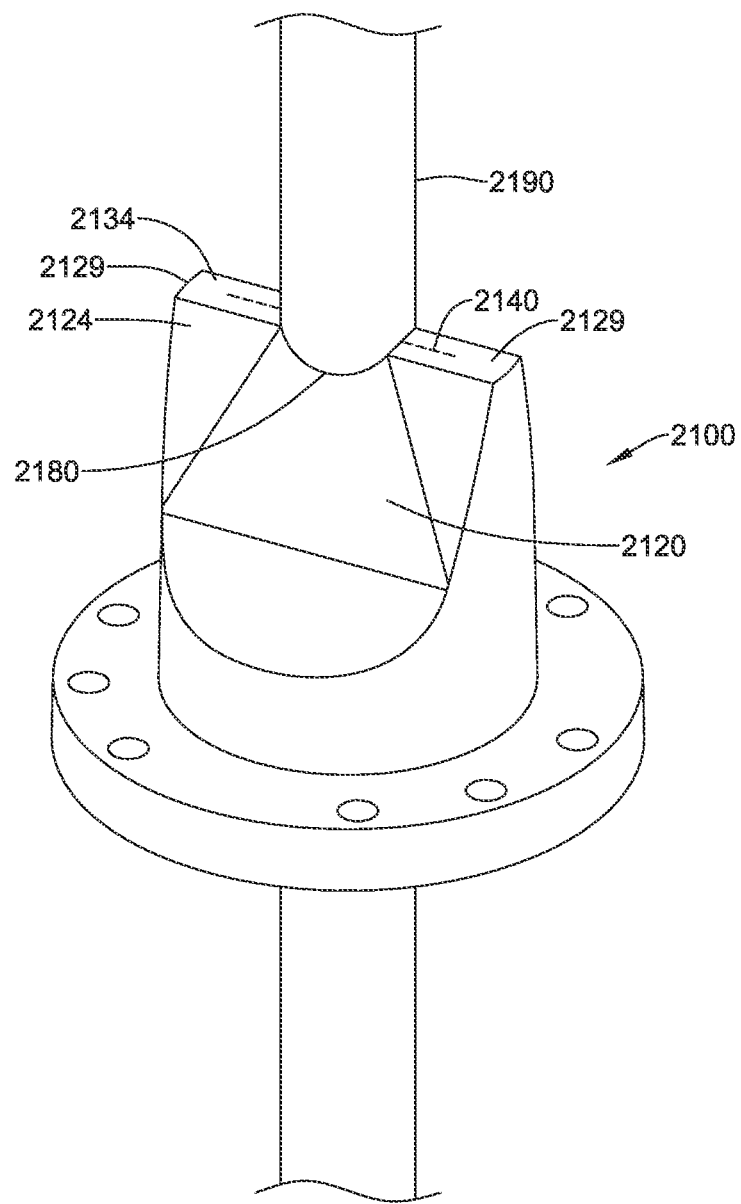
FIG. 28 is a perspective view of the valve of FIG. 23 with an instrument inserted therethrough.

As shown in the cross-sectional view of FIG. 26, the valve 2100 may define an axial passageway 2104 extending from the base 2110 to the lower end surface 2128 through the slit 2140 and the arcuate cutout 2180. The first ends 2122, 2132 of the first and second walls 2120, 2130 may define a curve adjacent the base 2110, as shown in FIG. 27. The inner surfaces 2121, 2131 of the first and second walls 2120, 2130 may be smooth and devoid of projections or depressions, if desired. As shown in FIG. 27, the first and second walls 2120, 2130 may each have a thickness 2125, 2135 that is constant from the first end 2122, 2132 to the second end 2124, 2134 of each wall, if desired. Furthermore, the wall thickness 2125, 2135 may also be constant from one end of the slit 2140, across the arcuate cutout 2180 to the other end of the slit, as shown in FIG. 26. The center plane 2145 of each wall 2120, 2130 may create this constant wall thickness. Turning to FIG. 28, when an instrument 2190 is inserted through the valve 2100 during use, the arcuate cutout 2180 may closely follow the perimeter of the instrument 2190 such that the edge of the arcuate cutout 2180 forms a fluid seal around the circumference of the instrument 2190. Furthermore, fluid within the surgical site may further exert radial pressure on the outside of the walls 2120, 2130, forcing the second ends 2124, 2134 together to seal the slit 2140 in the sections 2129 on either side of the arcuate cutout 2180, as shown in FIG. 28.

Figure 29:
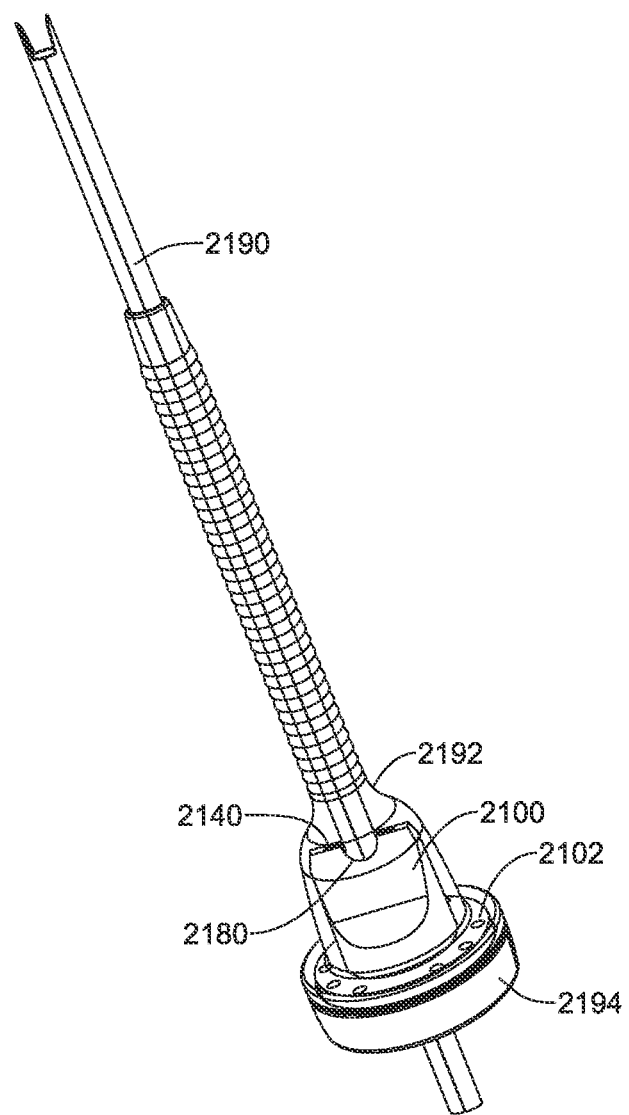
FIG. 29 is a perspective view of the valve of FIG. 23 in an access cannula.

FIG. 29 illustrates the valve 2100 in an access cannula 2192, with the flange 2102 of the valve 2100 attached to a cap 2194 of the cannula 2192. The cannula may include an elongate body defining an access lumen extending therethrough. The valve 2100 may be disposed within the access lumen. A medical device, illustrated as a tendon stapler 2190 that may be used in arthroscopic surgeries, is inserted through the access lumen of the cannula 2192. For example, the shaft of the tendon stapler 2190 may be inserted through the slit 2140 of the valve 2100, with the arcuate cutout 2180 sealing around the perimeter of the shaft of the tendon stapler 2190.

Figure 30:
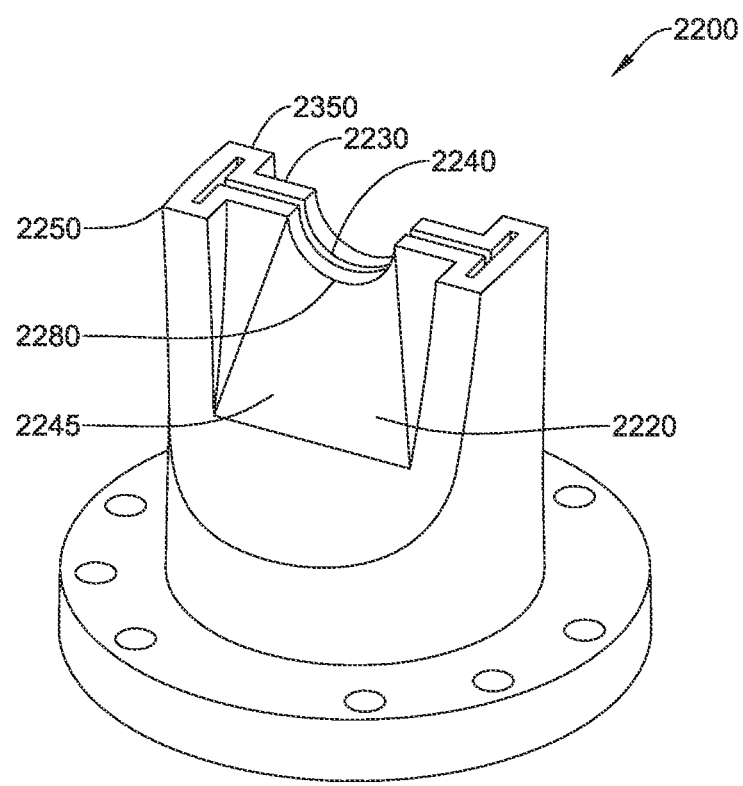
FIG. 30 is a perspective view of another exemplary valve.

FIG. 30 illustrates another variation of a duckbill valve 2200 including an arcuate cutout 2280. The lower end of the valve 2200 may have an H-shape when viewed from the bottom, as shown in FIG. 30. The first and second opposing walls 2220, 2230 have extensions 2250, 2350 on laterally opposite sides extending laterally away from the center plane 2245. Furthermore, the slit 2240 may have an H-shape, with opposing end segments of the slit 2240 extending perpendicular to the central portion of the slit 2240 traversing the arcuate cutout 2280. The end segments of the slit 2240 extend into the extensions 2250, 2350. The arcuate cutout 2280 may be similar to the arcuate cutout 2180 described above. Therefore, the above description of the arcuate cutout 2180 is also applicable to the arcuate cutout 2280, and thus will not be repeated. The arcuate cutout 2280 may function as described above, sealing around an instrument while the portions of the slit 2240 extending away from the arcuate cutout 2280 are pushed together to close the slit 2240 when fluid exerts radial pressure. All other features may be the same as described above for the valve 2100.

The valve 2100, 2200 may be made from a polymer material such as polyisoprene, to substantially reduce the amount of tearing or wear as a result of insertion and/or withdrawal of sharp instruments. Other natural or synthetic materials known to one of ordinary skill in the art, and that would substantially reduce the amount of tear or wear, could also be used for any or all of the elements of the valve 2100, 2200. These materials include, but are not limited to, silicone, rubber, vinyl, polyurethane elastomers, or a combination of components, including styreneethylene-butylene-styrene (SEBS) block co-polymers, polyolefins, mineral oils, and silicone oils.

The entire valve 2100, 2200 may be made as a single monolithic piece. In other examples, one or more of the flange 2102, body member 2105, base 2110, and first and second walls 2120, 2130 may be made of a different material and attached to the remaining elements, such as by heat seal, co-molding, over-molding, or adhesive.

Figure 31:
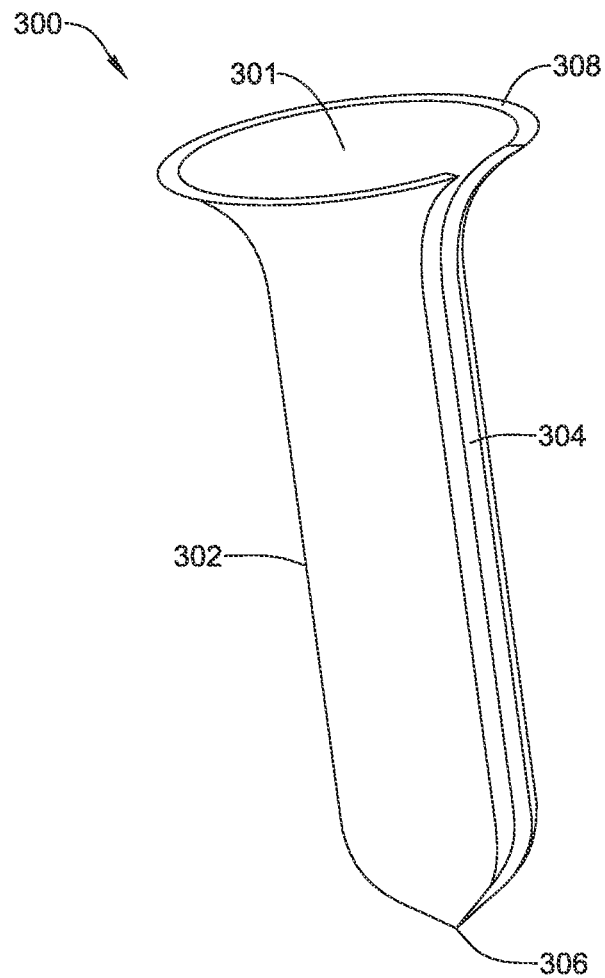
FIG. 31 is a perspective view of another exemplary cannula.
Figure 32:
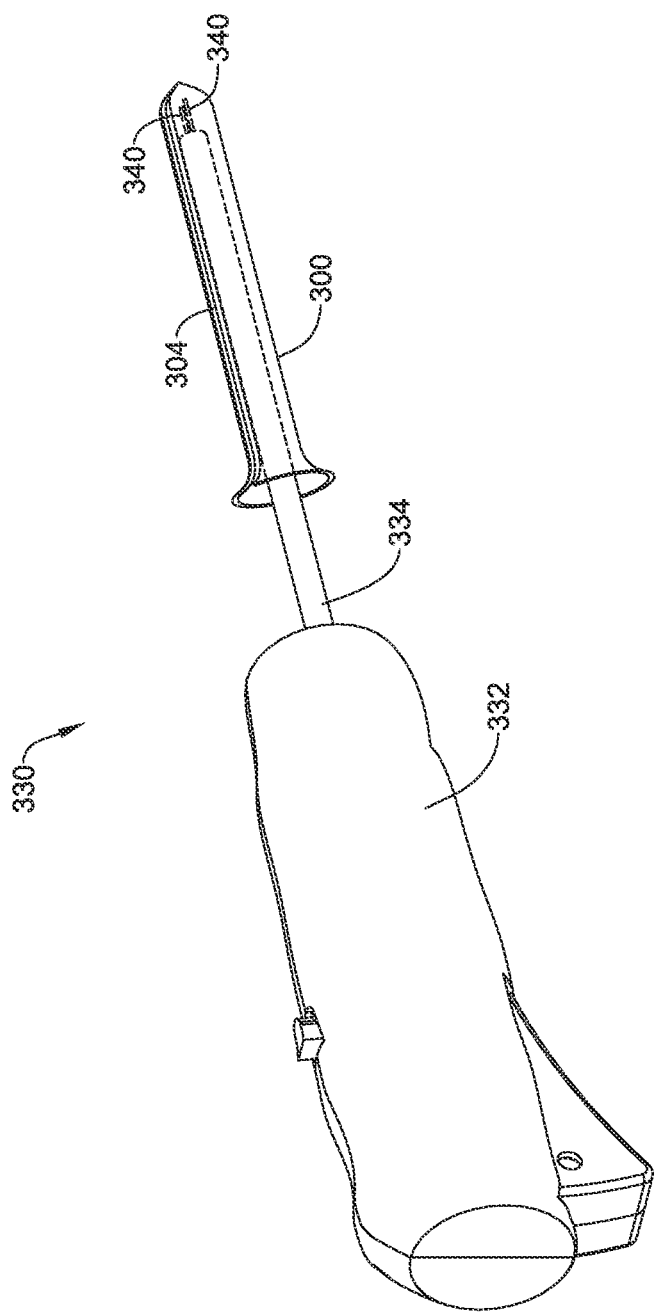
FIG. 32 is a perspective view of the cannula of FIG. 31 positioned on the shaft of a tissue stapler.

FIG. 31 illustrates another example cannula 300 configured to be used with a tissue stapler (e.g., tendon stapler), or other medical device, that allows for the insertion of the cannula 300 simultaneously with tissue stapler into the joint space for anchor deployment. The cannula 300 may include a flexible sheath 302 configured to surround the majority of the distal tip of the elongate shaft 334 of the tissue stapler 330, as shown in FIG. 32. The cannula 300 may include a lumen 301 extending therethrough with a slit 304 extending the entire length of the sheath 302, from the distal end 306 of the sheath 302 to the proximal end 308 of the sheath 302. The slit 304 allows for the cannula 300 to be placed around the shaft 334 by inserting the shaft 334 laterally through the slit 304 and to be removed laterally from the shaft 334 of the tissue stapler 330 by pulling the cannula 300 laterally relative to the shaft 334 such that the shaft 334 passes laterally out through the slit 304. In some examples, the tissue stapler 330 may be provided with the sheath 302 pre-assembled with the tissue stapler 330 such that the sheath 302 is surrounding the distal tip region of the shaft 334, as shown in FIG. 33A. Thus, the sheath 302 may surround and protect the prongs 340 of the tissue stapler 330 from contact with tissue 350 during insertion of the tissue stapler 300 through an incision. As shown in FIG. 33B, the combination tissue stapler 330 with attached cannula 300 may be inserted into an incision 352 through tissue 350 of the patient directly from the packaging, with the sheath 302 protecting the surrounding tissue while the shaft 334 of the tissue stapler 330 acts as an obturator.

Once the distal end 306 of the cannular 300 and the instrument contained therein are in the proper location, for example, in the shoulder joint space, the curved or flared proximal end 308 may be grasped and pulled proximally from exterior of the patient's body, such as exterior of an incision of the shoulder region. This pulls the sheath 302 back up the shaft 334 of the tissue stapler 330 with the slit 304 allowing for removal from the shaft 334 in a sideways or lateral manner, leaving the shaft 334 of the tissue stapler 330 within the patients' anatomy through the incision 352 alone without a cannula, as shown in FIG. 33C.

The proximal end 308 may have a flared region or petal shape, as illustrated in FIG. 31. The flared proximal end 308 may prevent the cannula 300 from being inserted into the incision and provide a lip for the user to grasp for withdrawal. In other examples, the distal end 306 of the cannula 300 may have a bullnosed recess that partially protects the sharp prongs 340 of the tissue stapler 330. The cannula 300 may provide the advantage of reducing the surgical steps when compared to the previously used cannula and providing protection from the prongs 340 of the tissue stapler 330 during insertion, as well as during packaging and back-table handoffs.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

What is claimed is:

1. A cannula for passing surgical instruments through tissue, comprising:
   an elongated body having a distal end, a proximal end, and a lumen extending along a longitudinal axis therebetween, wherein the elongated body is cylindrical and defined by a solid outer wall extending continuously around an entire circumference of the cylindrical elongated body and extending continuously axially from the distal end to the proximal end, the elongated body includes a plurality of circumferential ribs disposed on an outer surface of the elongated body;
   a flange extending radially outward from the distal end;
   a valve disposed within the lumen of the elongated body adjacent the proximal end;
   a cap configured to be disposed over the proximal end of the elongated body, the cap configured to secure the valve to the elongated body;
   a nut extending around a circumference of the elongated body and axially slidable along the elongate body, the nut configured to selectively engage the circumferential ribs to retain a position thereof;
   wherein the cap engages the valve to create a non-compressive seal therebetween;
   wherein a proximal surface of the valve has a first mating geometry and an inner surface of the cap has a second mating geometry, wherein the non-compressive seal is created between the valve and the cap when the first mating geometry of the valve engages the second mating geometry of the cap;
   wherein the first mating geometry of the valve includes at least one ridge and the second mating geometry of the cap includes at least two ridges separated by a channel, wherein when the cap engages the valve, the at least one ridge on the valve is received within the channel on the cap.

2. The cannula of claim 1, wherein the nut has a length measured parallel to the longitudinal axis of the elongate body, wherein the length is greater than a distance between two adjacent ones of the circumferential ribs.

3. The cannula of claim 1, wherein the flange has an outer diameter, and the nut extends radially outward from the longitudinal axis of the elongate body beyond the outer diameter of the flange.

4. The cannula of claim 1, wherein the nut has a proximal region and a distal region, the distal region having a radial outer extent greater than the proximal region.

5. A cannula for passing surgical instruments through tissue, comprising:
   an elongated body having a distal end, a proximal end, and a lumen extending along a longitudinal axis therebetween, wherein the elongated body is cylindrical and includes a plurality of circumferential ribs disposed on an outer surface of the elongated body;
   a flange extending radially outward from the distal end;
   a valve disposed within the lumen of the elongated body adjacent the proximal end;
   a cap configured to be disposed over the proximal end of the elongated body, the cap configured to secure the valve to the elongated body; and
   a nut extending around a circumference of the elongated body and axially slidable along the elongate body, the nut configured to selectively engage the circumferential ribs to retain a position thereof;
   wherein the cap is more flexible than the elongated body and the valve.

6. A cannula for passing surgical instruments through tissue comprising:
   an elongated body having a distal end, a proximal end, and a lumen extending along a longitudinal axis therebetween, wherein the elongated body is cylindrical and defined by a solid outer wall extending continuously around an entire circumference of the cylindrical elongated body and extending continuously axially from the distal end to the proximal end, the elongated body includes a plurality of circumferential ribs disposed on an outer surface of the elongated body;
   a flange extending radially outward from the distal end;
   a valve disposed within the lumen of the elongated body adjacent the proximal end;
   a cap configured to be disposed over the proximal end of the elongated body, the cap configured to secure the valve to the elongated body;
   a nut extending around a circumference of the elongated body and axially slidable along the elongate body, the nut configured to selectively engage the circumferential ribs to retain a position thereof;
   wherein the nut is configured to selectively engage the circumferential ribs and to move between a first position in which the nut is disengaged from the circumferential ribs, allowing the nut to slide axially along the elongated body, and a second position in which the nut engages the circumferential ribs;
   wherein the circumferential ribs are discontinuous and include at least one gap, the gaps of adjacent circumferential ribs aligned longitudinally along a portion of the elongated body, wherein the nut has an inner circumference sized to move over the circumferential ribs and at least one inwardly extending rigid projection, wherein when the nut is rotated such that the projection is aligned with the gaps, the nut slides axially along the elongated body, and when the nut is rotated such that the projection is not aligned with the gaps, the projection engages the circumferential ribs and prevents the nut from moving axially along the elongated body;
   and wherein a stop is disposed adjacent each gap, the stop configured to limit rotation of the projection.

* * * * *